(12) United States Patent
Lampilas et al.

(10) Patent No.: US 8,067,435 B2
(45) Date of Patent: Nov. 29, 2011

(54) NITROGEN-CONTAINING HETEROCYCLIC COMPOUNDS, THEIR PREPARATION AND THEIR USE AS ANTIBACTERIAL DRUGS

(75) Inventors: Maxime Lampilas, Paris (FR); David Rowlands, Poissy (FR); Benoit Ledoussal, Romainville (FR); Marie-Edith Gourdel, Romianville (FR); Emilie Renaud, Romainville (FR); Camille Pierres, Romainville (FR); Adel Kebsi, Romainville (FR)

(73) Assignee: AstraZeneca AB, Sodertalje (SE)

( * ) Notice: Subject to any disclaimer, the term of this patent is extended or adjusted under 35 U.S.C. 154(b) by 162 days.

(21) Appl. No.: 12/536,096

(22) Filed: Aug. 5, 2009

(65) Prior Publication Data
US 2010/0087648 A1    Apr. 8, 2010

(30) Foreign Application Priority Data
Oct. 3, 2008    (FR) .................................. 08 05 472

(51) Int. Cl.
*C07D 471/06*    (2006.01)
(52) U.S. Cl. ........................................ 514/300; 546/121
(58) Field of Classification Search .................. 514/300; 546/121
See application file for complete search history.

(56) References Cited

U.S. PATENT DOCUMENTS

| | | | |
|---|---|---|---|
| 6,841,562 B2 | 1/2005 | Badque et al. |
| 7,148,322 B2 | 12/2006 | Boffelli et al. |
| 7,232,833 B2 | 6/2007 | Bigot et al. |
| 7,232,834 B2 | 6/2007 | Bacque et al. |
| 7,439,253 B2 | 10/2008 | Lampilas et al. |
| 2002/0049192 A1 | 4/2002 | Ledoussal et al. |
| 2002/0173501 A1 | 11/2002 | Ledoussal et al. |
| 2003/0008894 A1 | 1/2003 | Ledoussal et al. |
| 2003/0171587 A1 | 9/2003 | Ledoussal et al. |
| 2003/0207862 A1 | 11/2003 | Ledoussal et al. |
| 2004/0029882 A1 | 2/2004 | Ledoussal et al. |
| 2004/0038975 A1 | 2/2004 | Ledoussal et al. |
| 2005/0020572 A1 | 1/2005 | Aszodi et al. |
| 2005/0101589 A1 | 5/2005 | Ledoussal et al. |
| 2005/0245747 A1 | 11/2005 | Bacon et al. |
| 2006/0100436 A1 | 5/2006 | Ledoussal et al. |
| 2009/0018329 A1 | 1/2009 | Lampilas et al. |
| 2009/0062284 A1 | 3/2009 | Bacon et al. |
| 2009/0111851 A1 | 4/2009 | Ledoussal et al. |
| 2010/0093784 A1* | 4/2010 | Ledoussal et al. ............ 514/300 |

FOREIGN PATENT DOCUMENTS

| | | |
|---|---|---|
| WO | WO/02/10172 | 2/2002 |
| WO | WO/02/100860 | 12/2002 |
| WO | WO/2004/022563 | 3/2004 |
| WO | WO/2004/052891 | 6/2004 |

* cited by examiner

Primary Examiner — D M Seaman
Assistant Examiner — Niloofar Rahmani

(57) ABSTRACT

The invention relates to nitrogen-containing heterocyclic compounds of general formula (I)

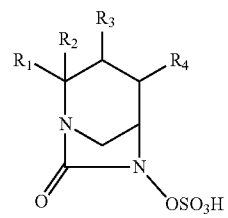

(I)

wherein:
$R_1$ represents a $(CH_2)_n$—$NH_2$ radical, n being equal to 1 or 2;
$R_2$ represents a hydrogen atom;
$R_3$ and $R_4$ form together a nitrogen-containing heterocycle with aromaticity with 5 apices containing 1, 2 or 3 nitrogen atoms, substituted on this nitrogen atom or one of these nitrogen atoms with a $(CH_2)_m$—$(C(O))_p$—$R_5$ group, m being equal to 0, 1, 2 or 3, p being equal to 0 or 1 and $R_5$ representing a hydroxy group, in which case p is equal to 1, or an amino, $(C_1$-$C_6)$alkyl or di-$(C_1$-$C_6)$alkyl amino, a nitrogen-containing heterocycle with aromaticity with 5 or 6 apices containing 1 or 2 nitrogen atoms and if necessary, an oxygen or sulfur atom;
it being understood that when the sub-group $(C(O))_p$—$R_5$ forms a carboxy, amino, $(C_1$-$C_6)$ alkyl or di-$(C_1$-$C_6)$ alkyl amino, group, m is different from 0 or 1;
in free form or as zwitterions and salts with pharmaceutically acceptable mineral or organic bases and acids, to their preparation and to their use as antibacterial drugs.

11 Claims, No Drawings

NITROGEN-CONTAINING HETEROCYCLIC COMPOUNDS, THEIR PREPARATION AND THEIR USE AS ANTIBACTERIAL DRUGS

CROSS-REFERENCE TO RELATED APPLICATIONS

This application claims priority to French Patent Application No. 08 05 472, filed Oct. 3, 2008, which is incorporated by reference herein.

BACKGROUND AND SUMMARY

The invention relates to nitrogen-containing heterocyclic compounds, to their preparation and to their use as antibacterial drugs.

The application WO 04/052891 notably describes compounds fitting the following formula:

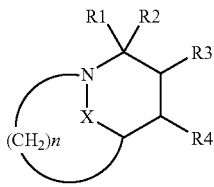

wherein:
$R_1$ represents a hydrogen atom, a COOH, COOR, CN, $(CH_2)_{n'}R_5$, $CONR_6R_7$ or radical

R is selected from the group formed by an alkyl radical containing 1 to 6 carbon atoms, optionally substituted with one or more halogen atoms or with a pyridyl radical, a —$CH_2$-alkenyl radical containing a total of 3 to 9 carbon atoms, a (poly)alkoxyalkyl group containing 1 to 4 oxygen atoms and 3 to 10 carbon atoms, an aryl radical containing 6 to 10 carbon atoms or an aralkyl radical containing 7 to 11 carbon atoms, the ring of the aryl or aralkyl radical being optionally substituted with an OH, $NH_2$, $NO_2$, alkyl radical containing 1 to 6 carbon atoms, an alkoxy radical containing 1 to 6 carbon atoms or with one or more halogen atoms,
$R_5$ is selected from the group formed by a COOH, CN, OH, $NH_2$, CO—$NR_6R_7$, COOR, OR radical, R being defined as above,
$R_6$ and $R_7$ are individually selected from the group formed by a hydrogen atom, an alkyl radical containing 1 to 6 carbon atoms, an alkoxy radical containing 1 to 6 carbon atoms, an aryl radical containing 6 to 10 carbon atoms and an aralkyl radical containing 7 to 11 carbon atoms and an alkyl radical containing 1 to 6 carbon atoms substituted with a pyridyl radical,
n' is equal to 1 or 2,
$R_3$ and $R_4$ form together a phenyl or a heterocycle with aromaticity with 5 or 6 apices containing 1 to 4 heteroatoms selected from nitrogen, oxygen and sulfur, substituted with one or more R' groups, R' being selected from the group formed by the —$(O)_a$—$(CH_2)_b$—$(O)_a$—$CONR_6R_7$, —$(O)_a$—$(CH_2)_b$—$OSO_3H$, —$(O)_a$—$(CH_2)_b$—$SO_3H$, —$(O)_a$—$SO_2R$, —$(O)_n$—$SO_2$—$CHal_3$, —$(O)_a$—$(CH_2)_b NR_6R_7$, —$(O)_a$—$(CH_2)_b$—NH—COOR, —$(CH_2)_b$—COOH, —$(CH_2)_b$—COOR, —OR", OH, —$(CH_2)_b$— phenyl radicals and $(CH_2)_b$-heterocycle with aromaticity with 5 or 6 apices containing 1 to 4 heteroatoms selected from nitrogen, oxygen and sulfur, the phenyl and the heterocycle being optionally substituted with one or more halogens, an alkyl containing 1 to 6 carbon atoms, an alkoxy containing 1 to 6 carbon atoms or $CF_3$, R, $R_6$ and $R_7$ being as defined earlier, R" being selected from the group formed by alkyl radicals containing 1 to 6 carbon atoms substituted with one or more hydroxy, protected hydroxy, oxo, halogen or cyano radicals, a being equal to 0 or 1 and b being an integer from 0 to 6, it being understood that when R' is OH, $R_1$ represents the radical $CONR_6R_7$ wherein $R_6$ or $R_7$ is an alkoxy containing 1 to 6 carbon atoms,
$R_2$ is selected from the group formed by a hydrogen atom, a halogen atom and R, $S(O)_mR$, OR, NHCOR, NHCOOR and $NHSO_2R$ radicals, R being as defined earlier and m being equal to 0, 1 or 2,
X represents a divalent group —C(O)—B— linked to the nitrogen atom through the carbon atom,
B represents a divalent group —O—$(CH_2)_{n"}$— linked to the carbonyl through the oxygen atom, a group —$NR_8$—$(CH_2)_{n"}$— or —$NR_8$—O— linked to the carbonyl through the nitrogen atom, n" is equal to 0 or 1 and $R_8$ is selected from the group formed by a hydrogen atom, an OH, R, OR, Y, OY, $Y_1$, $OY_1$, $Y_2$, $OY_2$, $Y_3$, O—$CH_2$—$CH_2$—$S(O)_m$—R, SiRaRbRc and OSiRaRbRc radical, Ra, Rb and Rc individually representing a linear or branched alkyl radical containing 1 to 6 carbon atoms or an aryl radical containing 6 to 10 carbon atoms, and R and m being defined as earlier,
Y is selected from the group formed by the COH, COR, COOR, $CONH_2$, CONHR, CONHOH, $CONHSO_2R$, $CH_2COOH$, $CH_2COOR$, CHF—COON, CHF—COOR, CF2-COOH, CF2-COOR, CN, $CH_2CN$, $CH_2CONHOH$, $CH_2CONHCN$, $CH_2$-tetrazole, $CH_2$-(protected tetrazole), $CH_2SO_3H$, $CH_2SO_2R$, $CH_2PO(OR)_2$, $CH_2PO(OR)(OH)$, $CH_2PO(R)(OH)$ and $CH_2PO(OH)_2$ radicals,
$Y_1$ is selected from the group formed by the $SO_2R$, $SO_2NHCOH$, $SO_2NHCOR$, $SO_2NHCOOR$, $SO_2NHCONHR$, $SO_2NHCONH_2$ and $SO_3H$ radicals,
$Y_2$ is selected from the group formed by the $PO(OH)_2$, $PO(OR)_2$, PO(OH)(OR) and PO(OH)(R) radicals,
$Y_3$ is selected from the group formed by the radicals, tetrazole, tetrazole substituted with the radical R, squarate, NH or NR tetrazole, NH or NR tetrazole substituted with the radical R, $NHSO_2R$ and $NRSO_2R$, $CH_2$-tetrazole and $CH_2$-tetrazole substituted with R, R being defined as above, and
n is equal to 1 or 2,
as well as the salts of these compounds with mineral or organic bases or acids.

The asymmetrical carbon atoms contained in the compounds of formula (I) may independently of each other have the R, S or RS configuration and the compounds of formula (I) therefore appear as pure enantiomers or pure diastereoisomers or as a mixture of enantiomers, notably of racemates, or mixtures of diastereoisomers. Further, the substituent $R_1$, $R_2$, or $R_4$ taken individually on the one hand and X on the other hand may be in the cis and/or trans position relatively to the ring on which they are attached, the compounds of formula (I) appear as cis isomers or trans isomers or mixtures thereof. Moreover, the application WO 02/100860 describes related compounds. The applicant has discovered that among the compounds described in the application WO 04/052891, certain particular compounds, none of which are described in the experimental part of this application, have quite unexpected antibacterial properties.

The unique character of the compounds of the invention lies in the fact that they have excellent activity on *Pseudomonas aeruginosa*, a bacterial strain frequently encountered in nocosomial infections as well as in patients suffering from cystic fibrosis. This interesting and unexpected activity is not present in compounds closest to them as prepared in the application WO 04/052891. It is illustrated later on in the experimental part.

Moreover, the compounds of the invention proved to be active on animal infection models, including on strains usually resistant to commonly used antibiotics. The compounds of the invention are capable of thwarting the main mechanisms of bacterial resistance which are β-lactamases, efflux pumps and mutations of porins.

The compounds of the invention are compounds fitting the formula above wherein $R_2$ represents a hydrogen atom, X represents a divalent group $C(O)NR_8$ wherein $R_8$ is a $OY_1$ radical, $Y_1$ being a $SO_3H$ radical, and especially including the following particular combination of substituents $R_1$, $R_3$, $R_4$: $R_1$ represents an alkyl radical substituted with an amino radical and $R_3$ and $R_4$ form together a nitrogen-containing heterocycle with aromaticity with 5 apices substituted with a group including or consisting in a polar substituent of the amino or aminated aromatic heterocycle or carboxy type.

The object of the invention is thus the compounds of general formula (I), in their possible isomer or diastereoisomer forms or mixtures:

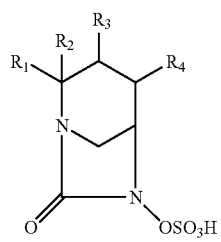

(I)

wherein:

$R_1$ represents a $(CH_2)_n$—$NH_2$ radical, n being equal to 1 or 2;

$R_2$ represents an hydrogen atom;

$R_3$ and $R_4$ form together a nitrogen-containing heterocycle with aromaticity with 5 apices containing 1, 2 or 3 nitrogen atoms, substituted on this nitrogen atom or on one of these nitrogen atoms with a $(CH_2)_m$—$(C(O))_p$—$R_6$ group, m being equal to 0, 1, 2 or 3, p being equal to 0 or 1 and $R_5$ representing a hydroxy group, in which case p is equal to 1, or an amino, $(C_1$-$C_6)$alkyl or di-$(C_1$-$C_6)$alkyl amino group, or a nitrogen-containing heterocycle with aromaticity with 5 or 6 apices containing 1 or 2 nitrogen atoms, and, if necessary, an oxygen or sulphur atom; it being understood that when the sub-group $(C(O))_p$—$R_6$ forms a carboxy, amino or $(C_1$-$C_6)$alkyl or di-$(C_1$-$C_6)$alkyl amino group, m is different from 0 or 1; in free form and as zwitterions and salts with pharmaceutically acceptable mineral or organic bases and acids.

By alkyl radical containing 1 to 6 carbon atoms, is notably meant the methyl, ethyl, propyl, isopropyl radical, as well as a linear or branched butyl, pentyl or hexyl radical. By heterocycle with aromaticity with 5 apices containing 1, 2 or 3 nitrogen atoms, are meant those selected in the following list, the two bonds symbolizing the junction with the nitrogen-containing ring formed by $R_3$ and $R_4$:

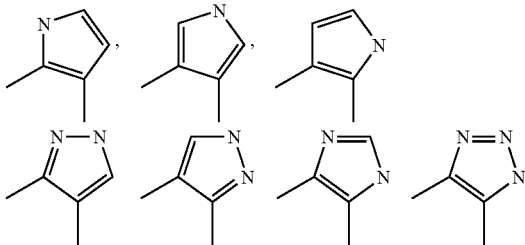

By nitrogen-containing heterocycle with aromaticity with 5 or 6 apices containing 1 or 2 nitrogen atoms and if necessary 1 oxygen or sulfur atom, are meant those of the type illustrated above, or an oxazole or thiazole ring, or a ring with 6 apices of the pyridine, pyrazine, pyrimidine or pyridazine type, the heterocycle being attached to the chain or to the heterocycle formed by $R_3$ and $R_4$ through a nitrogen atom or a carbon atom. Among the acid salts of the products of formula (I), mention may i.a. be made of those formed with mineral acids such as hydrochloric, hydrobromic, hydroiodic, sulfuric or phosphoric acids or with organic acids such as formic, acetic, trifluoroacetic, propionic, benzoic, maleic, fumaric, succinic, tartaric, citric, oxalic, glyoxylic, aspartic, alkane-sulfonic acids, such as methane- and ethane-sulfonic acids, arylsulfonic acids such as benzene- and para-toluene-sulfonic acids. Among the salts of the products of formula (I), mention may be made, i.a., of those formed with mineral bases such as for example, sodium, potassium, lithium, calcium, magnesium or ammonium hydroxide or with organic bases such as for example methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine, N-methylglucamine, or further phosphonium salts such as alkylphosphoniums, arylphosphoniums, alkylarylphosphoniums, alkenylaryl-phosphoniums, or quaternary ammonium salts such as tetra-n-butylammonium salts.

The asymmetrical carbon atoms contained in the compounds of formula (I) may independently of each other have the R, S or RS configuration and the compounds of formula (I) therefore exist as pure enantiomers or pure diastereoisomers or as a mixture of enantiomers, notably of racemates or mixtures of diastereoisomers. Further, the substituent $R_1$ on the one hand and the chain —C(O)—N($OSO_3H$)— on the other hand may be in the cis and/or trans position relatively to the ring on which they are attached, the compounds of formula (I) exist as cis isomers or trans isomers or mixtures.

Among the compounds of formula (I), the object of the invention is notably the compounds wherein $R_3$ and $R_4$ form together a substituted pyrazolyl heterocycle. Among the compounds of formula (I), the object of the invention is notably those wherein $R_1$ is a $(CH_2)_n$—$NH_2$ group, n being equal to 1 and the heterocycle formed by $R_3$ and $R_4$ is substituted with a $(CH_2)_m$—$(C(O))_p$—$R_5$ group as defined earlier, and more particularly among the latter, those wherein $R_5$ represents an amino, $(C_1$-$C_6)$alkyl or di-$(C_1$-$C_6)$alkyl amino, m and p being as defined earlier.

Among the compounds of formula (I), the object of the invention is most particularly the compounds described later on in the experimental part and notably those of the following names:

trans 8-(aminomethyl)-2-carbamoyle-4,8-dihydro-5-(sulfo-oxy)-4,7-methano-7H-pyrazolo[3,4-e][1,3]diazepin-6 (5H)-one, trans 8-(aminomethyl)-2-dimethylcarbamoyle-4,8-dihydro-5-(sulfooxy)-4,7-methano-7H-pyrazolo[3,4-e][1,3]diazepin-6(5H)-one, trans 8-(aminomethyl)-2-methylcarbamoyle-4,8-dihydro-5-(sulfooxy)-4,7-methano-7H-pyrazolo[3,4-e][1,3]diazepin-6(5H)-one, trans 8-(aminomethyl)-1-(2-aminoethyl)-4,8-dihydro-5-(sulfooxy)-4,7-methano-7H-pyrazolo[3,4-e][1,3]diazepin-6(5H)-one, trans 8-(aminomethyl)-2-(2-aminoethyl)-4,8-dihydro-5-(sulfooxy)-4,7-methano-7H-pyrazolo[3,4-e][1,3]diazepin-6(5H)—O-one, trans 8-(aminomethyl)-2-(2-pyridinyl)-4,8-dihydro-5-(sulfo-oxy)-4,7-methano-7H-pyrazolo[3,4-e][1,3]diazepin-6(5H)-one, trans [[8-(aminomethyl)-5,6-dihydro-6-oxo-5-(sulfooxy)-4H-4,7-methanopyrazolo[3,4-e][1,3]diazepin-2(8H)-acetic acid, trans 8-(aminomethyl)-5,6-dihydro-6-oxo-5-(sulfooxy)-4H-4,7-methanopyrazolo[3,4-e][1,3]diazepin-2(8H)-acetamide, in free form, as zwitterions and salt with pharmaceutically acceptable mineral or organic bases and acids, and as possible isomers or diastereoisomers, or mixtures.

Another object of the invention is a method for preparing compounds of formula (I), characterized in that a compound of formula (II) is treated:

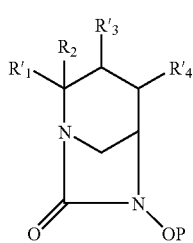

(II)

wherein represents an $R'_1$ radical wherein the nitrogen atom is protected, $R_2$ is as defined above, $R'_3$ and $R'_4$ form together a nitrogen-containing heterocycle with aromaticity with 5 apices containing 1, 2 or 3 nitrogen atoms and P represents a group protecting the hydroxy radical, in the presence of a base, with a compound of formula (III):

X—$(CH_2)_m$—$(C(O))_p$—$R'_5$ (III)

wherein X represents a halogen atom or an OH group which may be activated, m and p are as defined above and $R'_5$ represents an $R_5$ radical wherein the reactive amino or carboxy group is, if necessary, protected, in order to obtain a compound of formula (IV):

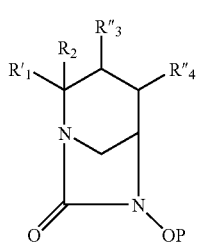

(IV)

wherein $R'_1$, $R_2$ and P are as defined above and $R''_3$ and $R''_4$ form together a nitrogen-containing heterocycle with aromaticity with 5 apices as defined above for $R_3$ and $R_4$, substituted with a $(CH_2)_m$—$(C(O))_p$—$R'_5$ group, m, p and $R'_5$ being as defined above, and the hydroxyl radical is then deprotected and the obtained compound is submitted to a sulfatation reaction by action of complexed $SO_3$, and then, if necessary the obtained compound is submitted to one or more of the following reactions, in a suitable order:

deprotection of the present aminated function(s) and if necessary of the carboxy group, salification, ion exchange, resolution or separation of diastereoisomers.

Preliminary protection of the amine at $R'_1$, and $R_{.5}$ is notably carried out in the form of benzylated or tritylated derivatives, of carbamates, notably allyl, benzyl, phenyl or tertbutyl carbamates, or further in the form of silylated derivatives such as tertbutyl dimethyl, trimethyl, triphenyl or further diphenyltertbutyl-silyl derivatives, or further phenylsulfonylalkyl or cyanoalkyl derivatives. Deprotection may be carried out with different methods known to one skilled in the art, depending on the nature of the protective group. It may notably be carried out through the action of an acid, for example trifluoroacetic acid, the deprotected compound being then obtained as a salt of the acid. It may further be carried out by hydrogenolysis or with soluble complexes of palladium(0) or through the action of tetrabutylammonium fluoride or by reduction. An illustration is provided further on in the experimental part.

The preliminary protection of the carboxy at $R'_{.5}$ is notably carried out in the form of derivatives of the ester type, notably alkyl, allyl, benzyl, benzhydryl or p-nitro benzyl esters. Deprotection may be carried out with different methods known to one skilled in the art, for example by saponification, acid hydrolysis, hydrogenolysis or cleavage with soluble complexes of palladium(0). The base in the presence of which the compound of formulae (II) and (III) are reacted may for example be an alkaline carbonate but other bases known to one skilled in the art may be used.

The preliminary protection of the hydroxyl of the compound of formula (II) is carried out in a standard way, in the form of ethers, esters or carbonates. The ethers may be alkyl or alkoxyalkyl ethers, preferably methyl or methoxyethoxmethyl ethers, aryl ethers, or preferably aralkyl ethers, for example benzyl ethers, or silylated ethers, for example the silylated derivatives mentioned above. The esters may be any cleavable ester known to one skilled in the art and preferably an acetate, propionate or benzoate or p-nitrobenzoate. The carbonates may for example be methyl, tertbutyl, allyl, benzyl or p-nitrobenzyl carbonates.

Deprotection is carried out with means known to one skilled in the art, notably saponification, hydrogenolysis, cleavage by soluble complexes of palladium(0), hydrolysis in an acid medium or further, for silylated derivatives treatment with tetrabutylammonium chloride, an illustration is provided further on in the experimental part. The possible activation of the hydroxyl of the compound of formula (III) is achieved in the form of a mesylate or tosylate, under conditions known to one skilled in the art. The sulfatation reaction is carried out by action of $SO_3$ complexes such as $SO_3$-pyridine or $SO_3$-dimethylformamide, by operating in pyridine or in dimethylformamide, the salt formed, for example the salt of pyridine, may be exchanged for example with a salt from another amine, a quaternary ammonium or an alkaline metal. An illustration is provided in the experimental part.

Salification by acids is if necessary carried out by adding an acid in a soluble phase to the compound. Salification by bases of the sulfo-oxy function may be achieved from the amine salt, and notably pyridine salt obtained during the action of the $SO_3$-amine complex and the other salts are obtained from this amine salt. It is notably possible to operate with ion exchange on a resin. The separation of the enantiomers and diastereoisomers may be achieved according to techniques known to one skilled in the art, notably chromatography either on a chiral phase or not. Examples of conditions which may be used are also described in application WO 04/052891 or further application WO 02/100860.

The compounds of formula (I) wherein n is equal to 0, p is equal to 1 and $R_5$ represents $R''_5$, $R''_5$ representing an amino, $(C_1-C_6)$ alkyl or di-$(C_1-C_6)$alkyl amino, may further be obtained by a method characterized in that a compound of formula (II) as defined above is treated in the presence of a base, with diphosgene and then with an amine of formula

wherein $R''_5$ has the values of $R_5$ above, in order to obtain a compound of formula (IV'):

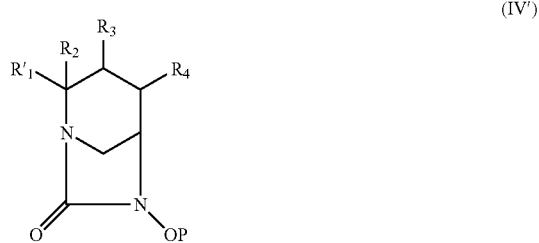

wherein $R'_1$, $R_2$ and P are as defined above and $R_3$ and $R_4$ form together a nitrogen-containing heterocycle with aromaticity with 5 apices as defined above, substituted with a —C(O)—$R''_5$ group, $R''_5$ being as defined above, and the synthesis is then continued as described above in the case of the compound of formula (IV).

The base used during the action of diphosgene may notably be a tertiary amine such as triethylamine. These same compounds of formula (I) may further if necessary be obtained with a method characterized in that a compound of formula (II) as defined above is treated with trimethylsilyl isocyanate or with an isocyanate of formula

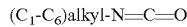

In order to obtain a corresponding compound of formula (IV), the synthesis is then continued as described above. The compounds of formula (I) wherein $R_5$ represents a heterocycle may be obtained with different reactions known to one skilled in the art for forming C—N bonds and notably by catalysis with palladium or copper as the one described in one of the examples hereafter.

As indicated above, the compounds of general formula (I) have excellent antibiotic activity on *Pseudomonas aeruginosa* as well as on animal infection models by strains resistant to commonly used antibacterial agents. This remarkable and unexpected antibiotic activity had not been observed for the compounds described in application WO 04/052891 and notably for the compounds structurally close to them. This is illustrated later on. These properties make said compounds suitable in the free form or as zwitterions or salts of pharmaceutically acceptable acids and bases, for use as drugs in treating severe infections by *Pseudomonas*, notably nosocomial infections and, generally, major infections in subjects at risks. These may in particular be infections of the respiratory tracts, for example acute pneumonia or chronic infections of the lower tracts, blood infections for example septicemias, acute or chronic infections of the urinary tracts, those of the auditory system, for example malign external otitis, or suppurating chronic otitis, those of the skin and of soft tissues, for example dermatitises, infected wounds, folliculitis, pyodermatis, stubborn forms of acne, eye infections, for example corneal ulcer, those of the nervous system, notably meningitises and brain abscesses, heart infections such as endocarditis, infections of bones and joints, such as stenoarticular pyoarthrosis, vertebral osteomyelitis, pubic symphysitis, infections of the gastro-intestinal tract, such as necrosing enterocolitis and perirectal infections.

Therefore the object of the present invention also is, in the form of drugs, and notably as antibiotic drugs, the compounds of formula (I) as defined above, in free form and as zwitterions and salts with pharmaceutically acceptable mineral or organic bases and acids. Among the compounds of formula (I), the object of the invention is notably the compounds, as drugs, wherein $R_3$ and $R_4$ form together a substituted pyrazolyl heterocycle. Among of the compounds of formula (I), the object of the invention is more particularly the compounds as drugs, wherein $R_1$ is a $(CH_2)_n$—$NH_2$ group, n being equal to 1 and the heterocycle formed by $R_3$ and $R_4$ is substituted with a $(CH_2)_m$—$(C(O))_p$—$R_5$ group as defined earlier, and more particularly among the latter, those in which $R_5$ represents an amino, $(C_1-C_6)$alkyl or di-$(C_1-C_6)$alkyl amino group, m and p being as defined earlier.

Among the compounds of formula (I), the object of the invention is most particularly the compounds, as a drug, with the following names:

trans 8-(aminomethyl)-2-carbamoyle-4,8-dihydro-5-(sulfooxy)-4,7-methano-7H-pyrazolo[3,4-e][1,3]diazepin-6(5H)-one, trans 8-(aminomethyl)-2-dimethylcarbamoyle-4,8-dihydro-5-(sulfooxy)-4,7-methano-7H-pyrazolo[3,4-e][1,3]diazepin-6(5H)-one, trans 8-(aminomethyl)-2-methylcarbamoyle-4,8-dihydro-5-(sulfooxy)-4,7-methano-7H-pyrazolo[3,4-e][1,3]diazepin-6(5H)-one, trans 8-(aminomethyl)-1-(2-aminoethyl)-4,8-dihydro-5-(sulfooxy)-4,7-methano-7H-pyrazolo[3,4-e][1,3]diazepin-6(5H)-one, trans 8-(aminomethyl)-2-(2-aminoethyl)-4,8-dihydro-5-(sulfooxy)-4,7-methano-7H-pyrazolo[3,4-e][1,3]diazepin-6(5H)-one, trans 8-(aminomethyl)-2-(2-pyridinyl)-4,8-dihydro-5-(sulfooxy)-4,7-methano-7H-pyrazolo[3,4-e][1,3]diazepin-6(5H)-one, trans [[8-(aminomethyl)-5,6-dihydro-6-oxo-5-(sulfooxy)-4H-4,7-methanopyrazolo[3,4-e][1,3]diazepin-2(8H)-acetic acid, trans 8-(aminomethyl)-5,6-dihydro-6-oxo-5-(sulfooxy)-4H-4,7-methanopyrazolo[3,4-e][1,3]diazepin-2(8H)-acetamide, in free form, as zwitterions and salts with pharmaceutically acceptable mineral or organic bases and acids, and in their possible isomer or diastereoisomer forms, or mixtures.

The object of the invention is also pharmaceutical compositions containing as an active ingredient, at least one of the compounds according to the invention as described above. These compositions may be administrated via a buccal, rectal, parenteral, notably intramuscular route, or via a local route, by topical application on the skin and mucosas. The compositions according to the invention may be solid or liquid and exist as pharmaceutical forms currently used in human medicine such as for example simple or sugar-coated tablets, gelatin capsules, granules, suppositories, injectable preparations, ointments, creams, gels; they are prepared according to the usual methods. The active ingredient(s) may be incorporated to excipients usually used in these pharmaceutical compositions, such as talc, gum arabic, lactose, starch, magnesium stearate, cocoa butter, aqueous carriers or not, fats of animal or plant origin, paraffinic derivatives, glycols, various wetting agents, dispersants or emulsifiers, preservatives. These compositions may notably exist as a lyophilisate intended to be dissolved extemporaneously in a suitable carrier, for example, apyrogenic sterile water.

The administered dose is variable depending on the treated disease, the subject in question, the administration route, and the relevant product. It may for example be comprised between 0.250 g and 10 g daily, orally in humans, with the product described in Examples 1, 4 or 5 or further comprised between 0.25 g and 10 g daily via an intramuscular or intravenous route. The products of formula (I) may also be used as disinfectants of surgical instruments.

DETAILED DESCRIPTION

The following examples illustrate the invention.

Example 1

Sodium trifluoroacetate salt of trans 8-(aminomethyl)-2-carbamoyle-4,8-dihydro-5-(sulfooxy)-4,7-methano-7H-pyrazolo[3,4-e][1,3]diazepin-6(5H)-one Stage A Trans-8-(hydroxymethyl)-4,8-dihydro-6-oxo-5-(phenylmethoxy)-4,7-methano-7H-pyrazolo[3,4-e][1,3]diazepin-6(5H)-one The ester, methyl trans-4,5,6,8-tetrahydro-6-oxo-5-(phenylmethoxy)-4,7-methano-7H-pyrazolo[3,4-e][1,3]diazepine-8-carboxylate described in the application WO2004/052891 (Example 1, stage K) (5 g, 15.2 mmol) is put into solution in an anhydrous methanol/tetrahydrofurane mixture 1/1 (100 mL), under nitrogen. NaBH4 (2.3 g, 60.9 mmol) is then added portionwise. After one night of stirring at room temperature, the reaction mixture is treated with a 10% $NaH_2PO_4$ aqueous solution (100 mL). After dry evaporation, the reaction medium is taken up into water. The formed precipitate is stirred for one night in ice, and then filtered and dried under reduced pressure in the presence of $P_2O_5$, in order to obtain the expected compound (3.30 g, 11.0 mmol, 72%) as a white powder.

MS (ES(+)): m/z [M+H]$^+$=301
$^1$H NMR (400 MHz, DMSO-d$_6$): δ (ppm)=3.18-3.50 (ABX, 2H, N—CH$_2$—CH—N), 3.65-3.76 (ABX, 2H, N—CH—CH$_2$—OH), 4.34 (t, 1H, N—CH—CH$_2$—OH), 4.46 (d, 1H, N—CH$_2$—CH—N), 4.88 (s, 2H, CH$_2$-Ph), 7.29-7.43 (m, 5H, Ph), 7.66 (s, 1H, H pyrazole), 12.72 (broad, 1H, OH).

Stage B 1,1-dimethyl Trans [[4,5,6,8-tetrahydro-6-oxo-5-(phenyl-methoxy)-4,7-methano-7H-pyrazolo[3,4-e][1,3]diazepin-8-yl]methyl]-carbamate The alcohol obtained in stage A of Example 1 (1.73 g, 5.76 mmol) is put into solution in anhydrous pyridine (35 mL) under nitrogen, at 0° C., and methanesulfonyl chloride (1.78 mL, 23 mmol) is then added dropwise. After 2 h 30 min of stirring at room temperature, the reaction medium is treated with a saturated ammonium chloride aqueous solution (100 mL), and then extracted with ethyl acetate. The combined organic phases are then washed with a saturated ammonium chloride aqueous solution, dried and then concentrated under reduced pressure in order to obtain the expected dimesylated derivative as a yellow oil.

The dimesylated intermediate is put into solution in anhydrous dimethylformamide (45 mL), under nitrogen, in the presence of sodium nitride (1.12 g, 17.3 mmol). The reaction mixture is heated to 70° C. for 24 h. 1 equivalent of nitride is added if necessary so that the conversion is complete. When the reaction is complete, the mixture is treated with a $NaH_2PO_4$ 10% aqueous solution (100 mL) and then extracted with dichloromethane. The combined organic phases are dried and then concentrated under reduced pressure in order to obtain the expected nitride as a yellow oil.

The intermediate is reacted under nitrogen in absolute ethanol (17.5 mL), and then di-tert-butyl dicarbonate (1.38 g, 6.34 mmol), triethylsilane (1.38 mL, 8.64 mmol) and 10% palladium hydroxide on coal (52 mg) are added successively. After one night at room temperature, the reaction mixture is filtered and then concentrated in order to obtain a crude yellow oil. This crude is purified by chromatography on a silica column (eluent: CH$_2$Cl$_2$/MeOH gradient 100/0 to 95/5 in 1% steps) in order to lead to the expected compound (1.36 g, 3.40 mmol, 34%) as a white solid.

MS (ES(+)): m/z [M+H]$^+$=401
$^1$H NMR (400 MHz, MeOH-d$_4$): δ (ppm)=1.51 (s, 9H, C(CH$_3$)$_3$), 3.21-3.59 (m, 4H, N—CH$_2$—CH—N et N—CH—CH$_2$—NHBoc), 4.36 (m, 1H, N—CH—CH$_2$—OH), 4.46 (m, 1H, N—CH$_2$—CH—N), 4.99 (AB, 2H, CH$_2$-Ph), 7.41-7.52 (m, 5H, Ph), 7.63 (s, 1H, H pyrazole).

Stage C 1,1-dimethylethyl trans [[2-carbamoyle-4,5,6,8-tetrahydro-6-oxo-5-(phenylmethoxy)-4,7-methano-7H-pyrazolo[3,4-e][1,3]diazepin-8-yl]methyl]-carbamate Under nitrogen, the amine obtained in stage B of Example 1 (100 mg, 0.250 mmol) is put into solution in dichloromethane). At 0° C., triethylamine (70 μL, 0.500 mmol) is added, followed by diphosgene (45 μL, 0.376 mmol) added rapidly dropwise. After 2 h 30 min of stirring at 0° C., ammonia (20% aqueous, 0.4 mL) is rapidly added and the medium is vigorously stirred at room temperature for 1 h. The medium is transferred into a separating funnel, rinsed with dichloromethane (5 mL), and then washed with a 10% sodium phosphate aqueous solution (10 mL). The aqueous phase is extracted with dichloromethane (10 mL). The organic phases are collected, washed with a saturated NaCl solution, dried and concentrated under reduced pressure in order to obtain after chromatography on a silica column (eluent: CH$_2$Cl$_2$/ethyl acetate 70/30), the expected derivative (94 mg, 0.212 mmol, 85%) as a beige solid.

MS (ES (+)): m/z [M+H]$^+$=443
$^1$H NMR (400 MHz, CDCl$_3$): δ (ppm)=1.44 (s, 9H, C(CH$_3$)$_3$), 3.09 (dd, 1H, N—CH$_2$—CH—N), 3.32 (m, 2H, CH—CH$_2$—NHBoc), 3.72 (dd, 1H, N—CH$_2$—CH—N), 3.98 (d, 1H, N—CH$_2$—CH—N), 4.59 (m, 1H, CH—CH$_2$—NHBoc), 4.92 (AB, 2H, N—O—CH$_2$-Ph), 5.93 (broad, 1H, NH), 6.95 (broad, 1H, NH), 7.37-7.41 (m, 5H, Ph), 8.03 (s, 1H, H pyrazole).

Stage D

Pyridinium salt of 1,1-dimethylethyl trans [[2-carbamoyle-4,5,6,8-tetrahydro-6-oxo-5-(sulfooxy)-4,7-methano-7H-pyrazolo[3,4-e][1,3]diazepin-8-yl]methyl]-carbamate Under nitrogen, the derivative obtained in stage C (94 mg, 0.212 mmol) is put into solution in dimethylformamide (0.3 mL) and dichloromethane (0.9 mL), and then 10% palladium on coal with 50% water (68 mg, 0.032 mmol) is added. After purging with vacuum/nitrogen, the reaction medium is placed under a hydrogen atmosphere until disappearance of the initial product in HPLC. The mixture is then concentrated in vacuo and then co-evaporated with anhydrous dichloromethane, finally dried under reduced pressure in the presence of $P_2O_5$ for 2 hrs, in order to obtain the expected debenzylated intermediate.

The debenzylated derivative is taken up in anhydrous pyridine (0.6 mL) in the presence of the pyridine/sulfur trioxide complex (68 mg, 0.425 mmol). The reaction medium is then stirred at room temperature until full conversion in HPLC, and then dry evaporated after treatment with additional water. The reaction crude is chromatographed on a silica column (eluent: $CH_2Cl_2$/MeOH gradient 100/0 to 80/20 in 5% steps) in order to obtain the expected product (50 mg, 0.093 mmol, 43%) as a white solid.

MS (ES (−)): m/z [M−]=431

$^1$H NMR (400 MHz, MeOH-$d_4$): δ (ppm)=1.52 (s, 9H, C($CH_3$)$_3$), 3.41-3.53, 3.62-3.75 (m, 4H, N—$CH_2$—CH—N et CH—$CH_2$—NHBoc), 4.64 (m, 1H, CH—$CH_2$—NHBoc), 4.98 (d, 1H, N—$CH_2$—CH—N), 8.00 (m, 2H, Py), 8.28 (s, 1H, H pyrazole), 8.74 (m, 1H, Py), 8.95 (m, 2H, Py).

Stage E

Sodium salt of 1,1-dimethylethyl trans [[2-carbamoyle-4,5,6,8-tetrahydro-6-oxo-5-(sulfooxy)-4,7-methano-7H-pyrazolo[3,4-e][1,3]diazepin-8-yl]methyl]-carbamate A suspension of 6 g of DOWEX 50WX8 resin in a 2N soda solution (30 mL) is stirred for 1 h, and then poured on a chromatography column. The column is conditioned with demineralized water up to a neutral pH, and then with a water/THF 90/10 mixture. The derivative obtained in stage D of Example 1 (49 mg, 0.091 mmol) is dissolved in a minimum of methanol, deposited on the column, and then eluted with a water/THF 90/10 mixture. The fractions containing the substrate are collected, frozen and freeze-dried in order to lead to the expected sodium salt (44 mg, 0.091 mmol, 100%) as a beige solid.

MS (ES (−)): m/z [M−H]$^-$=431

$^1$H NMR (400 MHz, MeOH-$d_4$): δ (ppm)=1.52 (s, 9H, C($CH_3$)$_3$), 3.41-3.53, 3.62-3.75 (m, 4H, N—$CH_2$—CH—N et CH—$CH_2$—NHBoc), 4.64 (m, 1H, CH—$CH_2$—NHBoc), 4.98 (d, 1H, N—$CH_2$—CH—N), 8.29 (s, 1H, H pyrazole).

Stage F

Sodium trifluoroacetate salt of trans 8-(aminomethyl)-2-carbamoyle-4,8-dihydro-5-(sulfooxy)-4,7-methano-7H-pyrazolo[3,4-e][1,3]diazepin-6(5H)-one A solution of trifluoroacetic acid (2.4 mL) in dichloromethane (2.4 mL) is added dropwise to a solution of the sodium salt obtained in stage E (42 mg, 0.092 mmol) in dichloromethane (1.2 mL) under nitrogen and cooled to 0° C. The reaction is held under stirring for 1 h at room temperature. The mixture is dry evaporated and taken up in water in order to obtain a beige precipitate. The precipitate is filtered, and then washed with ethanol in order to obtain the expected derivative (12 mg, 0.026 mmol, 28%) as a beige solid.

$^1$H NMR (400 MHz, DMSO-$d_6$): δ (ppm)=3.18 (m, 1H, N—$CH_2$—CH—N), 3.40-3.47 (m, 3H, N—$CH_2$—CH—N et CH—$CH_2$—$NH_3^+$), 4.68 (m, 1H, CH—$CH_2$—$NH_3^+$), 4.85 (d, 1H, N—$CH_2$—CH—N), 7.79 (broad, 1H, $CONH_2$), 7.87 (broad, 1H, $CONH_2$, 8.09 (broad, 3H, $NH_3^+$), 8.26 (s, 1H, H pyrazole).

Example 2

Sodium trifluoroacetate salt of trans 8-(aminomethyl)-2-dimethylcarbamoyle-4,8-dihydro-5-(sulfooxy)-4,7-methano-7H-pyrazolo[3,4-e][1,3]diazepin-6(5H)-one Stage A 1,1-dimethylentyl trans [[4,5,6,8-dihydro-2-dimethylcarbamoyle-6-oxo-5-(phenyl methoxy)-4,7-methano-7H-pyrazolo[3,4-e][1,3]diazepin-8-yl]methyl]-carbamate By proceeding as indicated in stage C of Example 1, the use of the derivative obtained in stage B of Example 1 (200 mg, 0.501 mmol), of dichloromethane (26 mL), of triethylamine (140 μL, 1.00 mmol), of diphosgene (91 μL, 0.751 mmol) and of dimethylamine (40 wt. % aqueous, 0.634 mL, 5.01 mmol) lead, after chromatography on a silica column (eluent: $CH_2Cl_2$/MeOH 99/1), to the expected derivative (170 mg, 0.361 mmol, 72%) as a beige solid.

MS (ES (+)): m/z [M+H]$^+$=471

$^1$H NMR (400 MHz, $CDCl_3$): δ (ppm)=1.20 (s, 9H, C($CH_3$)$_3$), 2.80 (dd, 1H, N—$CH_2$—CH—N), 2.93 (s, 6H, N($CH_3$)$_2$), 3.09 (m, 2H, CH—$CH_2$—NHBoc, N—$CH_2$—CH—N), 3.51 (m, 1H, CH—$CH_2$—NHBoc), 3.74 (d, 1H, N—$CH_2$—CH—N), 4.33 (m, 1H, CH—$CH_2$—NHBoc), 4.69 (AB, 2H, $CH_2$-Ph), 4.90 (broad, 1H, NH), 7.12-7.18 (m, 5H, Ph), 7.72 (s, 1H, H pyrazole).

Stage B

Pyridinium salt of 1,1-dimethylethyl trans [[4,5,6,8-tetrahydro-2-dimethylcarbamoyle-6-oxo-5-(sulfooxy)-4,7-methano-7H-pyrazolo[3,4-e][1,3]diazepin-8-yl]methyl]-carbamate By proceeding as indicated in stage D of Example 1, the use of the derivative obtained in stage A (176 mg, 0.374 mmol), of dimethylformamide (0.5 mL), of dichloromethane (1.6 mL) and of 10% palladium on coal with 50% water (119 mg, 0.032 mmol) lead to the expected debenzylated intermediate. The debenzylated intermediate, pyridine (1.1 mL) and the pyridine/sulfur trioxide complex (119 mg, 0.748 mmol) lead, after chromatography on a silica column (eluent: $CH_2Cl_2$/MeOH gradient 100/0 to 80/20 in 5% steps) to the expected derivative (167 mg, 0.309 mmol, 83%) as a beige solid.

MS (ES(−)): m/z [M−H]$^-$=459

$^1$H NMR (400 MHz, MeOH-$d_4$): δ (ppm)=1.52 (s, 9H, C($CH_3$)$_3$), 3.23 (s, 6H, N($CH_2$)$_2$), 3.41-3.53, 3.56-3.65 (m, 4H, N—$CH_2$—CH—N et CH—$CH_2$—NHBoc), 4.64 (m, 1H, CH—$CH_2$—NHBoc), 4.98 (d, 1H, N—$CH_2$—CH—N), 8.07 (m, 2H, Py), 8.20 (s, 1H, H pyrazole), 8.60 (m, 1H, Py), 8.88 (m, 2H, Py).

Stage C

Sodium trifluoroacetate salt of trans 8-(aminomethyl)-2-dimethylcarbamoyle-4,5,6,8-tetrahydro-5-(sulfooxy)-4,7-methano-7H-pyrazolo[3,4-e][1,3]diazepin-6(5H)-one By proceeding as indicated in stage E of Example 1, the use of the derivative obtained in stage B (167 mg, 0.309 mmol), of DOWEX 50WX8 resin (20 g) and of 2N soda (100 mL) lead to the expected sodium salt (139 mg, 0.288 mmol, 93%). By proceeding as indicated in stage F of Example 1, the sodium salt (139 mg, 0.288 mmol), dichloromethane (4 mL), trifluoroacetic acid (7.9 mL) in dichloromethane (7.9 mL) lead to the crude derivative which is taken up in water (~2 mL) and then frozen and freeze-dried in order to lead to the expected derivative (143 mg, 0.288 mmol, 100%) as a beige solid.

$^1$H NMR (400 MHz, DMSO-$d_6$): δ (ppm)=3.07 (s, 6H, N($CH_3$)$_2$), 3.23-3.27, 3.37-3.42 (m, 4H, N—$CH_2$—CH—N et CH—$CH_2$—$NH_3^+$), 4.68 (m, 1H, CH—$CH_2$—$NH_3^+$), 4.85 (d, 1H, N—$CH_2$—CH—N), 8.11 (broad, 3H, $NH_3^+$), 8.19 (s, 1H, H pyrazole).

Example 3

Sodium trifluoroacetate salt of trans 8-(aminomethyl)-2-methylcarbamoyl-4,8-dihydro-5-(sulfooxy)-4,7-methano-7H-pyrazolo[3,4-e][1,3]diazepin-6(5H)-one Stage A 1,1-dimethylethyl trans [[4,5,6,8-tetrahydro-2-methylcarbamoyl-6-oxo-5-(phenylmethoxy)-4,7-methano-7H-pyrazolo[3,4-e][1,3]diazepin-8-yl]methyl]-carbamate By proceeding as indicated in stage C of Example 1, the reaction applying the derivative obtained in stage B of Example 1 (200 mg, 0.501 mmol), dichloromethane (26 mL), triethylamine (140 μL, 1.00 mmol), diphosgene (91 μL, 0.751 mmol) and a methylamine solution (40 wt % aqueous, 0.437 mL, 5.01 mmol) is repeated twice. The crude products are grouped and lead after chromatography on a silica column ($CH_2Cl_2$/AcOEt 100/0 to 80/20), to the expected derivative (170 mg, 0.372 mmol, 60%).

MS (ES(+): m/z [M+H]$^+$=457

$^1$H NMR (400 MHz, CDCl$_3$): δ (ppm)=1.49 (s, 9H, C(CH$_3$)$_3$), 3.02 (d, 3H, NH—CH$_3$), 3.10 (AB, 1H, N—CH$_2$—CH—N), 3.34-3.38 (m, 2H, N—CH$_2$—CH—N et CH—CH$_2$—NHBoc), 3.8 (broad, 1H, CH—CH$_2$—NHBoc), 4.00 (d, 1H, N—CH$_2$—CH—N), 4.56-4.60 (m, 1H, CH—CH$_2$—NHBoc), 4.88-5.06 (AB, 2H, N—O—CH$_2$-Ph), 5.10 (broad, 1H, NH), 6.95 (broad, 1H, NH), 7.42-7.75 (m, 5H, Ph), 8.07 (s, 1H, H pyrazole).

Stage B

Pyridinium salt of 1,1-dimethylethyl trans [[4,5,6,8-tetrahydro-2-methylcarbamoyl-6-oxo-5-(sulfooxy)-4,7-methano-7H-pyrazolo[3,4-e][1,3]diazepin-8-yl]methyl]-carbamate By proceeding as indicated in stage D of Example 1, application of the derivative obtained in stage A (160 mg, 0.350 mmol), dimethylformamide (0.51 mL), dichloromethane (1.52 mL), 10% palladium on coal with 50% water (112 mg, 0.052 mmol) and hydrogenation for 2 h 15 min lead to the expected debenzylated intermediate.

Application of the debenzylated intermediate of pyridine (1.0 mL) and of pyridine/sulfur trioxide complex (111 mg, 0.699 mmol) lead, after chromatography on a silica column conduit, (eluent: $CH_2Cl_2$/MeOH 100/0 to 80/20), to the expected derivative (120 mg, 0.224 mmol, 64%) as a beige solid.

MS (ES(+): m/z [M+H]$^+$=447) et (ES(−)): m/z [M−H]$^-$=445

$^1$H NMR (400 MHz, CDCl$_3$): δ (ppm)=1.48 (s, 9H, C(CH$_3$)$_3$), 3.01 (d, 3H, NH—CH$_3$), 3.25 (broad, 1H, N—CH$_2$—CH—N), 3.40 (broad, 1H, CH—CH$_2$—NHBoc), 3.7 (broad, 1H, N—CH$_2$—CH—N), 3.85 (broad, 1H, CH—CH$_2$—NHBoc) 4.60 (broad, 1H, —CH$_2$—CH—N), 5.03 (s, 1H, CH—CH$_2$—NHBoc), 5.40 (broad, 1H, NH), 7.10 (broad, 1H, NH), 7.87-7.91 (m, 2H, Pyridine), 8.20 (s, 1H, H pyrazole), 8.36 (t, 1H, Pyridine), 8.94 (d, 2H, pyridine).

Stage C

Sodium salt of 1,1-dimethylethyl trans [[4,5,6,8-tetrahydro-2-methylcarbamoyl-6-oxo-5-(sulfooxy)-4,7-methano-7H-pyrazolo[3,4-e][1,3]diazepin-8-yl]methyl]-carbamate By proceeding as indicated in stage E of Example 1, application of the derivative obtained in stage B (120 mg, 0.228 mmol) deposited in a minimum of water, of DOWEX 50WX8 resin (20 g) and of 2N soda (70 mL) leads to the expected sodium salt (100 mg, 0.213 mmol, 93%) as a white lyophilisate.

MS (ES(−)): m/z [M−H]$^-$=445

$^1$H NMR (400 MHz, D$_2$O): 1.48 (s, 9H, C(CH$_3$)$_3$), 2.85 (s, 3H, NH—CH$_3$), 3.40-3.70 (m, 4H, N—CH$_2$—CH—N et CH—CH$_2$—NHBoc), 4.60 (m, 1H, N—CH$_2$—CH—N), 5.10 (s, 1H, CH—CH$_2$—NHBoc), 8.23 (s, 1H, H pyrazole).

Stage D

Sodium trifluoroacetate salt of trans 8-(aminomethyl)-2-methylcarbamoyl-4,8-dihydro-5-(sulfooxy)-4,7-methano-7H-pyrazolo[3,4-e][1,3]diazepin-6(5H)-one By proceeding as indicated in stage F of Example 1, application of the sodium salt obtained in stage C ((94 mg, 0.2 mmol), of dichloromethane (3 mL) and of trifluoroacetic acid (2 mL) leads to the crude derivative which is taken up in water (10 mL) and then frozen and freeze-dried. The expected derivative is obtained (95 mg, 0.196 mmol, 98%) as a brown solid.

MS (ES(−)): m/z [M−H]$^-$=345 et ES(+): m/z [M+H]$^+$=447

$^1$H NMR (400 MHz, DMSO-$d_6$+1 goutte D$_2$O): 3.77 (s, 3H, NH—CH$_3$); 3.22-3.48 (m, 4H, N—CH$_2$—CH—N et CH—CH$_2$—NHBoc), 4.66-4.70 (m, 1H, N—CH$_2$—CH—N), 4.84 (s, 1H, CH—CH$_2$—NHBoc), 8.23 (s, 1H, H pyrazole).

Example 4

Sodium trifluoroacetate salt of trans 8-(aminomethyl)-1-(2-amino-ethyl)-4,8-dihydro-5-(sulfooxy)-4,7-methano-7H-pyrazolo[3,4-e][1,3]diazepin-6(5H)-one

Stage A

Methyl trans-1-(2-tert-butoxycarbonylamino-ethyl)-4,5,6,8-tetrahydro-6-oxo-5-(phenylmethoxy)-4,7-methano-7H-pyrazolo[3,4-e][1,3]diazepine-8-carboxylate, methyl trans-2-(2-tert-butoxycarbonylamino-ethyl)-4,5,6,8-tetrahydro-6-oxo-5-(phenylmethoxy)-4,7-methano-7H-pyrazolo[3,4-e][1,3]diazepine-8-carboxylate The ester, methyl trans-4,5,6,8-tetrahydro-6-oxo-5-(phenylmethoxy)-4,7-methano-7H-pyrazolo[3,4-e][1,3]diazepine-8-carboxylate, described in application WO2004/052891 (Example 1, stage K) (1.13 g, 3.44 mmol) is put into solution in anhydrous dimethylformamide (4.0 mL) in the presence of potassium carbonate (712 mg, 5.16 mmol) and of 2-(boc-amino)-ethyl bromide (770 mg, 3.44 mmol). The reaction medium is heated to 55° C. Additional amounts of $K_2CO_3$ (2×712 mg, 2×5.16 mmol) and of bromide (2×770 mg, 2×3.44 mmol) are added after 4 hrs and 14 additional hours. The reaction is further continued for 8 hrs at 55° C. The suspension is cooled, filtered and rinsed with ethylacetate. The organic phase is washed with 10% tartaric acid solution and then dried and concentrated under reduced pressure. The crude is purified by chromatography on silica (eluent: gradient $CH_2Cl_2$/MeOH 100/0 to 90/10) in order to lead to the N1-substituted derivative (380 mg, 0.81 mmol, 23%) as well as to the N2-substituted isomer (475 mg, 1.01 mmol, 29%).

N1-Substituted Derivative:
MS (ES(+)): m/z [M+H]$^+$=472
$^1$H NMR (400 MHz, CDCl$_3$): δ (ppm)=1.45 (s, 9H, C(CH$_3$)$_3$), 3.24 (d, 1H, N—CH$_2$—CH—N), 3.42 (dd, 1H, N—CH$_2$—CH—N), 3.50 (m, 1H, CH$_2$—CH$_2$—NHBoc), 3.60 (m, 1H, CH$_2$—CH$_2$—NHBoc), 3.86 (s, 3H, CH$_3$), 3.98 (d, 1H, N—CH$_2$—CH—N), 4.09 (m, 2H, CH$_2$—CH$_2$—NHboc), 4.95 (AB, 2H, CH$_2$-Ph), 5.19 (broad, 1H, NH), 5.23 (s, 1H, CH—CO$_2$Me), 7.39-7.44 (m, 6H, H pyrazole+Ph).

N2-Substituted Derivative:
MS (ES(+)): m/z [M+H]$^+$=472
$^1$H NMR (400 MHz, CDCl$_3$): δ (ppm)=1.45 (s, 9H, C(CH$_3$)$_3$), 3.48-3.53 (m, 4H, N—CH$_2$—CH—N, CH$_2$—$\overline{CH_2}$—NHBoc), 3.85 (s, 3H, CH$_3$), $\overline{3.97}$ (d, 1H, N—CH$_2$—$\overline{CH}$—N), 4.18 (m, 2H, CH$_2\overline{CH_2}$—NHboc), 4.95 (AB, 2H, $\overline{CH_2}$-Ph), 5.29 (s, 1H, $\underline{CH}$—$\overline{CO_2}$Me), 7.25 (s, 1H, H pyra$\overline{zole}$), 7.38-7.43 (massive, 5H, Ph).

Stage B

Trans 1-(2-tert-butoxycarbonylamino-ethyl)-8-(hydroxymethyl)-4,5,6,8-teetrahydro-5-(phenylmethoxy)-4,7-methano-7H-pyrazolo[3,4-e][1,3]diazepin-6(5H)-one By proceeding as indicated in stage A of Example 1, application of the N1-substituted ester obtained in stage A (475 mg, 1.0 mmol), of NaBH$_2$ (76 mg+76 mg, 2.0 mmol+2.0 mmol), of tetrahydrofurane (12.5 mL) and of methanol (12.5 mL) at 0° C. leads, after chromatography on a silica column (eluent: gradient CH$_2$Cl$_2$/MeOH 100/0 to 90/10) to the expected derivative (321 mg, 0.72 mmol, 72%).

$^1$H NMR (400 MHz, CDCl$_3$): δ (ppm)=1.42 (s, 9H, C(CH$_3$)$_3$)), 3.26-3.32 (m, 3H, N—CH$_2$—CH—N, CH$_2$—CH$_2$—NHBoc), 3.50 (m, 2H, N—CH$_2$—CH—N, CH$_2$—CH$_2$—NHboc), 3.95 (d, 1H, N—CH$_2$—CH—N), 4.06 (m, 3H, CH$_2$—CH$_2$—NHBoc, CH—CH$_2$—OH), 4.62 (m, 1H, CH—CH$_2$—OH), 4.95 (AB, 2H, CH$_2$-Ph), 5.28 (broad, 1H, NH), 7.36-7.44 (m, 6H, Ph+H pyrazole).

Stage C 1,1-dimethyl trans [[1-(2-tert-butoxycarbonylamino-ethyl)-4,5,6,8-tetrahydro-6-oxo-5-(phenylmethoxy)-4,7-methano-7H-pyrazolo[3,4-e][1,3]diazepin-8-yl]methyl]-carbamate By proceeding as indicated in stage B of Example 1, the application of the alcohol obtained in stage B (320 mg, 0.72 mmol) in dichloromethane (20 mL), of methanesulfonyl chloride (83 μL+55 μL, 1.08 mmol+0.72 mmol) and of triethylamine (151 μL+100 μL, 1.08 mmol+0.72 mmol) leads, after purification by chromatography on a silica column (eluent: gradient CH$_2$Cl$_2$/MeOH 100/0 to 90/10) to the expected mesylated derivative (229 mg, 0.44 mmol, 61%).

$^1$H NMR (400 MHz, CDCl$_3$): δ (ppm)=1.46 (s, 9H, C(CH$_3$)$_3$), 3.17 (s, 3H SO$_2$Me), 3.23 (d, 1H, N—CH$_2$—CH—N), 3.37 (dd, 1H, N—CH$_2$—CH—N), 3.54 (m, 2H CH$_2$—CH$_2$—NHBoc), 3.97 (d, 1H, N—CH$_2$—CH—N), 4.07 (m, 2H, CH$_2$—CH$_2$—NHBoc), 4.62 (m, 2H, CH$_2$—OMs), 4.87 (m, 1H, CH—CH$_2$—OMs), 4.95 (AB, 2H, CH$_2$-Ph) 5.06 (broad, 1H, NH), 7.38-7.45 (m, 6H, Ph, H pyrazole).

The mesylated intermediate (300 mg, 0.575 mmol) in dimethylformamide (4 mL) and NaN$_3$ (75 mg+75 mg, 1.15 mmol+1.15 mmol) lead to the expected azide.

$^1$H NMR (400 MHz, CDCl$_3$): δ (ppm)=1.43 (s, 9H, C(CH$_3$)$_3$), 3.24 (d, 1H, N—CH$_2$—CH—N), 3.31 (dd, 1H, N—CH$_2$—CH—N), 3.49 (m, 2H, CH$_2$—CH$_2$—NHBoc), 3.75 (m, 2H, CH$_2$—N$_3$), 3.94 (d, 1H, N—CH$_2$—CH—N), 3.99 (m, 2H, CH$_2$—CH$_2$—NHBoc), 4.68 (dd, 1H, CH—CH$_2$—N$_3$), 4.91 (AB, 2H, CH$_2$-Ph), 5.17 (broad, 1H, NH), 7.33-7.41 (m, 6H, Ph, H pyrazole).

Trimethylphosphine (1M solution in tetrahydrofurane, 748 μL, 0.75 mmol) is added at 0° C. to a solution of the azide obtained above (320 mg, 0.575 mmol) in tetrahydrofurane (2.5 mL) and toluene (2.5 mL). This solution is stirred for 2 hrs at room temperature, and then cooled down to 0° C. and a solution of BOC—ON (212 mg, 0.86 mmol) in tetrahydrofurane (2 mL) is added. The solution is stirred for 1 h at room temperature, and then hydrolyzed by adding a saturated NaHCO3 solution and then extracted with ethyl acetate. The collected organic phases are dried and then concentrated. The residue is purified by chromatography on silica column (eluent: gradient cyclohexane/ethyl acetate 60/40 to 30/70) in order to provide the expected derivative (220 mg, 0.41 mmol, 70%).

MS (ES(+)): m/z [M+H]$^+$=543
$^1$H NMR (400 MHz, CDCl$_3$): δ (ppm)=1.44 (s, 9H, C(CH$_3$)$_3$), 1.45 (s, 9H, C(CH$_3$)$_3$), 3.13 (d, 1H, N—CH$_2$—CH—N), 3.25 (m, 2H, N—CH$_2$—CH—N, CH—CH$_2$—NHBoc), 3.56 (m, 2H, CH$_2$—CH$_2$—NHBoc), 3.75 (m, 1H, CH—CH$_2$—NHBoc), 3.95 (d, 1H, N—CH$_2$—CH—N), 4.11 (m, 2H, CH$_2$—CH$_2$—NHBoc), 4.55 (dd, 1H, CH—CH$_2$—NHBoc), 4.92 (AB, 2H, CH$_2$-Ph), 5.29 (broad, 2H, NH), 7.35-7.43 (m, 6H, Ph, H pyrazole).

Stage D

Sodium trifluoroacetate salt of trans 8-(aminomethyl)-1-(2-amino-ethyl)-4,8-dihydro-5-(sulfooxy)-4,7-methano-7H-pyrazolo[3,4-e][1,3]diazepin-6(5H)-one By proceeding as indicated in stage D of Example 1, the application of the compound obtained in stage C (210 mg, 0.387 mmol) in dimethylformamide (1 mL) and of dichloromethane (3 mL), Pd/C (50% $H_2O$, 75 mg+40 mg) leads to the expected debenzylate derivate.

The application of the debenzylated intermediate, of the pyridine/sulfur trioxide complex (123 mg, 0.775 mmol) and of pyridine (2 mL) leads after purification by chromatography on a silica column (eluent: gradient $CH_2Cl_2$/MeOH 100/0 to 80/20), to the expected pyridium salt (230 mg, 0.387 mmol, 100%).

By proceeding as indicated in stage C of Example 2, the application of the pyridinium salt obtained above (230 mg, 0.387 mmol), of a 2N soda solution (50 mL) and of DOWEX 50WX8 resin (18 g) leads to the expected sodium salt (121 mg, 0.22 mmol, 56%) as a white powder.

MS (ES(−)): m/z [M−H]$^−$=531

$^1$H NMR (400 MHz, DMSO-d$_6$): δ (ppm)=1.37 (s, 9H, C(CH$_3$)$_3$), 1.41 (s, 9H, C(CH$_3$)$_3$), 3.20-3.33 (m, 5H, N—CH$_2$—CH—N, CH—CH$_2$—NHBoc, CH$_2$—CH$_2$—NHBoc), 3.43 (m, 1H, CH—CH$_2$—NHBoc), 3.99 (m, 3H, CH$_2$—CH$_2$—NHBoc), 4.44 (dd, 1H, CH—CH$_2$—NHBoc), 4.65 (d, 1H, N—CH$_2$—CH—N), 6.92 (broad, 1H, NH), 7.11 (broad, 1H, NH), 7.43 (s, 1H, H pyrazole).

The application of the sodium salt (55 mg, 0.099 mmol) in dichloromethane (1.5 mL) and of a mixture of trifluoroacetic acid (3 mL) and of dichloromethane (3 mL) leads to the expected sodium trifluoroacetate salt (47 mg, 0.081 mmol, 70%) as a cream-colored powder.

$^1$H NMR (400 MHz, DMSO-d$_6$): δ (ppm)=3.26-3.42 (m, 6H, N—CH$_2$—CH—N, CH—CH$_2$—NH$_3$$^+$, CH$_2$—CH$_2$—NH$_3$$^+$), 4.23 (m, 2H, CH$_2$—CH$_2$—NH$_3$$^+$), 4.78 (m, 2H, CH—CH$_2$—NH$_3$$^+$, N—CH$_2$—CH—N), 7.60 (s, 1H, H pyrazole), 8.02 (broad, 3H, NH$_3$$^+$), 8.19 (broad, 3H, NH$_3$$^+$).

Example 5

Sodium trifluoroacetate salt of trans 8-(aminomethyl)-2-(2-amino-ethyl)-4,8-dihydro-5-(sulfooxy)-4,7-methano-7H-pyrazolo[3,4-e][1,3]diazepin-6(5H)-one Stage A Trans-2-(2-tert-butoxycarbonylamino-ethyl)-8-(hydroxymethyl)-4,8-dihydro-5-(phenylmethoxy)-4,7-methano-7H-pyrazolo[3,4-e][1,3]diazepin-6(5H)-one By proceeding as indicated in stage A of Example 1, the application of the N2-substituted ester obtained in stage A of Example 4 (623 mg, 1.32 mmol), of NaBH$_4$ (300 mg, 7.92 mmol), of tetrahydrofurane (13 mL) and of methanol (13 mL) to 0° C. leads, after chromatography on a silica column (eluent: $CH_2Cl_2$/MeOH 98/2 to 90/10) to the expected derivative (250 mg, 0.58 mmol, 43%).

MS (ES(+)): m/z [M+H]$^+$=444

$^1$H NMR (400 MHz, CDCl$_3$): δ (ppm)=1.40 (s, 9H, C(CH$_3$)$_3$), 3.24 (d, 1H, N—CH$_2$—CH—N), 3.31 (dd, 1H, N—CH$_2$—CH—N), 3.35 (m, 1H, CH$_2$—CH$_2$—NHBoc), 3.48 (m, 1H, CH$_2$—CH$_2$—NHBoc), 3.89-4.11 (m, 5H, CH$_2$—CH$_2$—NHBoc, N—CH$_2$—CH—N, CH—CH$_2$—OH), 4.61 (dd, 1H, N—CH—CH$_2$—N), 4.92 (AB, 2H, CH$_2$-Ph), 5.18 (broad, 1H, NH), 7.21 (s, 1H, H pyrazole), 7.33-7.42 (m, 5H, Ph).

Stage B 1,1-dimethyl trans [[2-(2-tert-butoxycarbonylamino-ethyl)-4,5,6,8-tetrahydro-6-oxo-5-(phenylmethoxy)-4,7-methano-7H-pyrazolo[3,4-e][1,3]diazepin-8-yl]methyl]-carbamate By proceeding as indicated in stage C of Example 4, the application of the alcohol obtained in stage A (450 mg, 1.05 mmol) in dichloromethane (30 mL), of methanesulfonyl chloride (131 µL, 1.68 mmol) and of triethylamine (237 µL 1.68 mmol) leads to the expected mesylated derivative (532 mg, 1.02 mmol 97%).

MS (ES(+)): m/z [M+H]$^+$=522

$^1$H NMR (400 MHz, CDCl$_3$): δ (ppm)=1.45 (s, 9H, C(CH$_3$)$_3$), 3.15 (s, 3H. SO$_2$CH$_3$), 3.20 (d, 1H, N—CH$_2$—CH—N), 3.40 (dd, 1H, N—CH$_2$—CH—N), 3.50 (m, 2H. CH$_2$—CH$_2$—NHboc), 3.98 (d, 1H, N—CH$_2$—CH—N), 4.13 (m, 2H, CH$_2$—CH$_2$—NHBoc), 4.61 (m, 2H, CH$_2$—OMs), 4.88 (m, 1H, CH—CH$_2$—OMs), 4.95 (AB, 2H, CH$_2$-Ph), 7.24 (s, 1H, H pyrazole), 7.37-7.45 (m, 5H, Ph).

The application of the mesylated intermediate (532 mg, 1.05 mmol) in dimethylformamide (7.5 mL) and of NaN$_3$ (615 mg, 9.45 mmol) leads to the expected azide (566 mg, 1.05 mmol).

$^1$H NMR (400 MHz, CDCl$_3$): δ (ppm)=1.41 (s, 9H, C(CH$_3$)$_3$)), 3.20 (d, 1H, N—CH$_2$—CH—N), 3.35 (dd, 1H, N—CH$_2$—CH—N), 3.44 (m, 2H, CH$_2$—CH$_2$—NHBoc), 3.65 (m, 2H, CH$_2$—N$_3$), 3.95 (d, 1H, N—CH$_2$—CH—N), 4.09 (m, 2H, CH$_2$—CH$_2$—NHBoc), 4.71 (dd, 1H, CH—CH$_2$—N$_3$), 4.92 (AB, 2H, CH$_2$-Ph), 4.98 (broad, 1H, NH), 7.21 (s, 1H, H pyrazole), 7.33-7.41 (m, 5H, Ph).

The application of the azide above (565 mg, 1.05 mmol), of trimethylphosphine (1M solution in tetrahydrofurane, 1.36 mL, 1.36 mmol), of BOC—ON (388 mg, 1.58 mmol), of tetrahydrofurane (5.5 mL) and of toluene (3 mL) leads to the expected product (205 mg, 0.38 mmol, 36%).

MS (ES(+)): m/z [M+H]$^+$=543

$^1$H NMR (400 MHz, CDCl$_3$): δ ppm)=1.45 (s, 9H, C(CH$_3$)$_3$), 1.46 (s, 9H, C(CH$_3$)$_3$), 3.10 (d, 1H N—CH$_2$—CH—N), 3.29 (dd, 1H, N—CH$_2$—CH—N), 3.37 (m, 1H, CH—CH$_2$—NHBoc), 3.49 (m, 2H, CH$_2$—CH$_2$—NHBoc), 3.69 (m, 1H, CH—CH$_2$—NHBoc), 3.94 (d, 1H, N—CH$_2$—CH—N), 4.10 (m, 2H, CH$_2$—CH$_2$—NHBoc), 4.58 (dd, 1H, CH—CH$_2$—NHBoc), 4.91 (broad, 1H, NH), 4.92 (AB, 2H, CH$_2$-Ph), 5.13 (broad, 1H, NH), 7.20 (s, 1H, H pyrazole), 7.37-7.44 (m, 5H, Ph).

Stage C

Sodium trifluoroacetate salt of trans 8-(aminomethyl)-2-(2-amino-ethyl)-4,8-dihydro-5-(sulfooxy)-4,7-methano-7H-pyrazolo[3,4-e][1,3]diazepin-6(5H)-one By proceeding as indicated in stage D of Example 1, the application of the compound obtained in stage B (85 mg, 0.157 mmol) in a dimethylformamide/dichloromethane mixture (1/3, 2 mL) and of Pd/C (50% $H_2O$, 30 mg) leads to the expected debenzylated derivative.

The application of the obtained debenzylated intermediate, of the pyridine/sulfur trioxide complex (50 mg, 0.314 mmol) and of pyridine (0.75 mL) leads, after purification by chromatography on a silica column (eluent: gradient CH$_2$Cl$_2$/MeOH 98/2 to 80/20), to the expected pyridinium salt (85 mg, 0.139 mmol, 86%).

By proceeding as indicated in stage C of Example 2, the application of the pyridinium salt (85 mg, 0.139 mmol), of a 2N soda solution (42 mL) and of DOWEX 50WX8 (8.5 g) leads to the expected sodium salt (75 mg, 0.135 mmol, 86%), as a cream-colored powder.

MS (ES(−)): m/z [M$^-$]=531

$^1$H NMR (400 MHz, DMSO-d$_6$): δ (ppm)=1.37 (s, 9H, C(CH$_3$)$_3$), 1.40 (s, 9H, C(CH$_3$)$_3$)), 3.17-3.32 (m, 5H, N—CH$_2$—CH—N, CH—CH$_2$—NHBoc, CH$_2$—CH$_2$—NHBoc), 3.60 (m, 1H, CH—CH$_2$—NHBoc), 4.04 (m, 2H, CH—CH$_2$—NHBoc), 4.31 (dd, 1H, CH—CH$_2$—NHBoc), 4.65 (s, 1H, N—CH$_2$—CH—N), 6.94 (broad, 2H, NH), 7.65 (s, 1H, H pyrazole).

The application of the sodium salt (75 mg, 0.135 mmol) in dichloromethane (2 mL) and of a mixture of trifluoroacetic acid (4 mL) and of dichloromethane (4 mL) leads to the sodium trifluoroacetate salt (35 mg, 0.059 mmol, 44%) as a cream-colored powder.

$^1$H NMR (400 MHz, DMSO-d$_6$): δ (ppm)=3.20-3.41 (m, 6H, N—CH$_2$—CH—N, CH—CH$_2$—NNH$_3^+$, CH$_2$—CH$_2$—NH$_3^+$), 4.30 (m, 2H, CH$_2$—CH$_2$—NH$_3^+$), 4.63 (dd, 1H, CH—CH$_2$—NH$_3^+$), 4.77 (d, 1H, N—CH$_2$—CH—N), 7.85 (s, 1H, H pyrazole), 8.04 (broad, 3H, NH$_3^+$), 8.17 (broad, 3H, NH$_3^+$).

Example 6

Sodium trifluoroacetate salt of trans 8-(aminomethyl)-2-(2-pyridinyl)-4,8-dihydro-5-(sulfooxy)-4,7-methano-7H-pyrazolo[3,4-e][1,3]diazepin-6(5H)-one Stage A 1,1-dimethylethyl trans [[4,5,6,8-tetrahydro-2-(2-pyridinyl)-6-oxo-5-(phenylmethoxy)-4,7-methano-7H-pyrazolo[3,4-e][1,3]diazepin-8-yl]methyl]-carbamate The derivative obtained in stage B of Example 1 (0.500 g, 1.248 mmol), 2-bromopyridine (217 mg, 1.373 mmol), L-proline (32 mg, 0.275 mmol), copper iodide (24 mg, 0.125 mmol) and potassium carbonate (345 mg, 2.497 mmol) are suspended in anhydrous dimethylsulfoxide (1.875 mL). The reaction is then continued under nitrogen, in a sealed tube at 100° C. for 48 hrs. The reaction medium is then treated with water and then extracted with dichloromethane. The organic phase is then dried and concentrated. The thereby obtained crude product is then purified by chromatography on silica (eluent: CH$_2$Cl$_2$/MeOH 98/2 and then 95/5) in order to obtain the expected product (91 mg, 0.189 mmol, 15%).

MS (ES(+)): m/z [M+H]$^+$=477

$^1$H NMR (400 MHz, MeOD-d$_4$): δ (ppm)=1.51 (s, 9H, tBu), 3.37-3.39 (m, 4H, N—CH$_2$—CH—N, N—CH—CH$_2$—NHBOC), 4.44 (d, 1H, N═CH—CH$_2$—NHBOC), 4.65 (dd, 1H, N—CH$_2$—CH—N), 4.98 (AB, 2H, CH$_2$Ph), 7.25-7.53 (m, 6H, Ph, pyridine), 7.90 (m, 2H, pyridine), 8.42 (d, 1H, pyridine), 8.51 (s, 1H, pyrazole).

Stage B

Sodium salt of 1,1-dimethylethyl trans [[4,5,6,8-tetrahydro-2-(2-pyridinyl)-6-oxo-5-(sulfooxy)-4,7-methano-7Hpyrazolo[3,4-e][1,3]diazepin-8-yl]methyl]carbamate By proceeding as indicated in stage D of Example 1, application of the derivative obtained in stage A (90 mg, 0.189 mmol), of a dimethylformamide/dichloromethane 1/3 mixture (2.0 mL) and of 10% palladium on coal with 50% water (36 mg) leads after 3 days under hydrogen to the expected benzylated intermediate.

The application of the debenzylated intermediate, of pyridine (0.73 mL) and of pyridine/sulfur trioxide complex (60 mg, 0.378 mmol) leads, after chromatography on a silica column (eluent: CH$_2$Cl$_2$/MeOH 90/10), to the expected derivative (63 mg).

The crude is then taken up in pyridine (0.73 mL), under nitrogen, in the presence of the SO$_3$/pyridine complex (60 mg, 0.378 mmol). The reaction medium is then stirred at room temperature until complete conversion in HPLC (72 hrs). After treatment by adding H2O, the mixture is filtered and then dry-evaporated. The thereby obtained crude product is purified by chromatography on silica (eluent: CH$_2$Cl$_2$/MeOH 90/10). The product is thus obtained pure (63 mg).

A suspension of 8.5 g of DOWEX 50WX8 resin in a 2N soda solution (43 mL) is stirred for 1 h, and then poured on a chromatography column. The column is conditioned with demineralized water up to a neutral pH. The obtained derivative (63 mg) is dissolved in a minimum of methanol and water, deposited on the column and then eluted with H$_2$O. The fractions contained in the substrate are collected, frozen and freeze-dried in order to lead to the expected sodium salt (55 mg, 0.112 mmol, 60%) as a yellow powder.

MS (ES (−)): m/z [M−H]$^-$=465

$^1$H NMR (400 MHz, MeOD-d$_4$): δ (ppm)=1.53 (s, 9H, $^t$Bu), 1.54 (m, 4H, N—CH$_2$—CH—N, N—CH—CH$_2$—NHBoc), 4.58 (dd, 2H, N═CH—CH$_2$—NHBoc), 5.02 (d, 1H, N—CH$_2$—CH—N), 7.34 (m, 1H, pyridine), 7.97 (m, 2H, pyridine), 8.47 (d, 1H, pyridine), 8.65 (s, 1H, H pyrazole).

Stage C

Sodium trifluoroacetate salt of trans 8-(aminomethyl)-2-(2-pyridinyl)-4,8-dihydro-5-(sulfooxy)-4,7-methano-7H-pyrazolo[3,4-e][1,3]diazepin-6(5H)-one By proceeding as indicated in stage F of Example 1, the application of the sodium salt obtained in step B (55 mg, 0.112 mmol), of anhydrous dichloromethane (1.92 mL), and of a trifluoroacetic acid/dichloromethane 1/1 mixture (7.68 mL) leads to a crude derivative which is taken up in water and then washed with diethyl ether. The insoluble product is filtered and dried under reduced pressure in order to obtain the expected product (20 mg, 0.04 mmol, 35%) as a beige powder.

MS (ES (+)): m/z [M+H]$^+$=367

$^1$H NMR (400 MHz, DMSO-d$_6$): δ (ppm)=3.30-3.49 (2 ABX, 4H, N—CH$_2$—CH—N, N—CH—CH$_2$—NH$_3^+$), 4.75 (dd, 2H, N—CH═CH$_2$—NH$_3^+$), 4.92 (m, 1H, N—CH$_2$—CH—N), 7.35 (m, 1H, pyridine), 7.83 (d, 1H, pyridine), 7.95 (m, 1H, pyridine), 8.49 (m, 1H, pyridine), 8.61 (s, 1H, H pyrazole).

Example 7

Sodium trifluoroacetate salt of trans-8-(aminomethyl)-5,6-dihydro-6-oxo-5-(sulfooxy)-4H-4,7-methanopyrazolo[3,4-e][1,3]diazepin-2(8H)-acetic acid

Stage A

1,1-dimethylethyl trans-5,6-dihydro-8-(tert-butoxycarbonyl-aminomethyl)-6-oxo-5-(phenylmethoxy)-4H-4,7-methano-pyrazolo[3,4-e][1,3]diazepine-2(8H)acetate The derivative obtained in stage B of Example 1 (0.200 g, 0.5 mmol) is put into solution in anhydrous dimethylformamide (0.5 mL), and then tert-butyl bromoacetate (234 mg, 1.2 mmol) and potassium carbonate (138 mg, 1 mmol) are added. The reaction is then continued under nitrogen, in a sealed tube at 75° C. The reaction is followed with HPLC. When the conversion is complete, the reaction medium is treated with $H_2O$ and then extracted with dichloromethane. The combined organic phases are then dried on sodium sulfate, filtered and then concentrated. The thereby obtained crude product is then purified by chromatography on silica (eluent: gradient CH2Cl2/MeOH 100/0 to 95/5) in order to obtain the expected product (186 mg, 0.36 mmol, 72%) as a mixture of 2 N1/N2 isomers in a ratio of about 1/2.
N2 Isomer:
$^1$H NMR (400 MHz, DMSO-$d_6$): δ (ppm)=1.41 (s, 18H, C($CH_3$)$_3$), 3.19-3.32 (m, 4H, N—$CH_2$—CH—N, N—CH—$CH_2$—NHBoc), 4.30 (dd, 1H, N═CH—$CH_2$—NHBoc), 4.49 (m, 1H, N—$CH_2$—CH—N), 4.85 (s, 2H, $CH_2CO_2$tBu), 4.89 (s, 2H, $CH_2$Bn), 6.95 (m, 1H, NHBOC), 7.36-7.43 (m, 5H, Ph), 7.68 (s, 1H, pyrazole).

Stage B

Sodium salt of 1,1-dimethylethyl trans-5,6-dihydro-8-(tert-butoxycarbonylaminomethyl)-6-oxo-5-(sulfooxy)-4H-4,7-methanopyrazolo[3,4-e][1,3]diazepine-2(8H)acetic acid The compound obtained in stage A (186 mg, 0.362 mmol) is put into solution in a dichloromethane/dimethylformamide 3/1 mixture (4.12 mL). After purging with vacuum/nitrogen, the 10% palladium on coal with 50% water (74 mg) is added. After again purging with vacuum/nitrogen, the reaction mixture is placed under hydrogen and stirred at room temperature. Progression of the reaction is followed with HPLC. After disappearance of the initial product (3 h 30 min), the mixture is concentrated, co-evaporated with anhydrous dichloromethane, finally placed under reduced pressure in the presence of $P_2O_5$ for 1 h. The crude is then taken up in pyridine (1.39 mL), under nitrogen, in the presence of the $SO_3$/pyridine complex (115 mg, 0.724 mmol). The reaction medium is then stirred at room temperature until complete conversion in HPLC (24 hrs). After treatment by adding $H_2O$, the mixture is filtered and dry-evaporated. The thereby obtained crude product is purified by chromatography on silica (eluent: gradient $CH_2Cl_2$/MeOH 95/5 to 80/20). The expected product is thereby obtained (117 mg).
A suspension of 20 g of DOWEX 50WX8 resin in a 2N soda solution (100 mL) is stirred for 1 h, and then poured on a chromatography column. The column is conditioned with demineralized water up to a neutral pH. The obtained derivative (117 mg, 0.233 mmol) is dissolved in a minimum of water, deposited on the column, and then eluted with $H_2O$. The fractions containing the substrate are collected, frozen and freeze-dried in order to lead to the expected sodium salt (66 mg, 0.126 mmol, 35%) as a white powder.
N2 Isomer:
MS (ES (-)): m/z [M–H]$^-$=502
$^1$H NMR (400 MHz, DMSO-$d_6$): δ(ppm)=1.42 (s, 9H, C($CH_3$)$_3$), 3.20-3.35 (m, 4H, N—$CH_2$—CH—N, N—CH—$CH_2$—NHBoc), 4.32 (dd, 2H, N═CH—$CH_2$—NHBoc), 4.81 (m, 1H, N—$CH_2$—CH—N), 4.85 (s, 2H, $CH_2CO_2C(CH_3)_3$), 6.99 (m, 1H, NHBOC), 7.67 (s, 1H, pyrazole).

Stage C

Sodium trifluoroacetate salt of trans-8-(aminomethyl)-5,6-dihydro-6-oxo-5-(sulfooxy)-4H-4,7-methanopyrazolo[3,4-e][1,3]diazepine-2(8H)acetic acid By proceeding as indicated in stage F of Example 1, the application of the sodium salt obtained in stage B (66 mg, 0.126 mmol), of anhydrous dichloromethane (2.3 mL), and of a trifluoroacetic acid/dichloromethane 1/1 mixture (9.2 mL) leads to the crude derivative which is taken up in water and then washed with ether and hexane. The aqueous phase is then frozen and then freeze-dried in order to lead to the expected product (54 mg, 0.111 mmol, 88%) as a yellow solid. The product consists of a mixture of N1/N2 isomers in a ratio of 28/72.
N2 Ilsome
MS (ES (-)): m/z [M–H]$^-$=346
$^1$H NMR (400 MHz, MeOD-$d_4$): δ (ppm)=3.36-3.56 (m, 4H, N—$CH_2$—CH—N, N—CH—$CH_2$—$NH_3^+$), 4.78 (dd, 1H, N═CH—$CH_2$—$NH_3^+$), 4.92 (dd, 1H, N—$CH_2$—CH—N), 4.99 (s, 2H, $CH_2CO_2$H), 7.80 (s, 1H, pyrazole).

Example 8

Sodium trifluoroacetate salt of trans-8-(aminomethyl)-5,6-dihydro-6-oxo-5-(sulfooxy)-4H-4,7-methanopyrazolo[3,4-e][1,3]diazepin-2(8H)-acetamide

Stage A

Trans-5,6-dihydro-8-(tert-butoxycarbonylaminomethyl)-6-oxo-5-(phenylmethoxy)-4H-4,7-methanopyrazolo[3,4-e][1,3]diazepine-2(8H)acetamide The derivative obtained in stage B of Example 1 (1 g, 2.5 mmol) is put into solution in anhydrous dimethylformamide (2.5 mL). 2-bromoacetamide (829 mg, 6 mmol) and potassium carbonate (692 mg, 5 mmol) are added. The reaction is stirred, under nitrogen in a sealed tube at 75° C. 2-bromoacetamide (1 eq.) and $K_2CO_3$ (1 eq.) are added after one night, and the reaction is continued for 4 days (~60% conversion). The reaction medium is treated with $H_2O$ and then extracted with dichloromethane. The combined organic phases are then dried on sodium sulfate, filtered and then concentrated. The thereby obtained crude product is purified by chromatography on silica (eluent: gradient $CH_2Cl_2$/MeOH 100/0 to 95/5) in order obtain the expected product (188 mg, 0.41 mmol, 16%) as a mixture of N1/N2 isomers in a ratio of about 1/2.

N2 Isomer:

MS (ES (+)): m/z [M+H]$^+$=457

$^1$H NMR (400 MHz, DMSO-d$_6$): δ (ppm)=1.39 (s, 9H, C(CH$_3$)$_3$), 3.12-3.33 (m, 4H, N—CH$_2$—CH—N, N—CH—CH$_2$—NHBoc), 4.31 (m, 1H, N—CH—CH$_2$—NHBoc), 4.40 (m, 1H, N—CH$_2$—CH—N), 4.66 (s, 2H, CH$_2$CONH$_2$), 4.89 (s, 2H, CH$_2$Bn), 6.99 (m, 1H, NHBOC), 7.58-7.62 (m, 5H, Ph), 7.66 (s, 1H, pyrazole).

Stage B

Sodium salt of trans-5,6-dihydro-8-(tert-butoxycarbonyl-aminomethyl)-6-oxo-5-(sulfooxy)-4H-4,7-methano-pyrazolo[3,4-e][1,3]diazepine-2(8H)acetamide By proceeding as in stage B of Example 7, the compound obtained in stage A (188 mg, 0.411 mmol) is hydrogenated, and then sulfated in the presence of SO$_3$/pyridine complex (131 mg, 0.823 mmol) in pyridine (1.58 mL), under nitrogen at room temperature for 4 days. The obtained crude product is purified by chromatography on silica (eluent: gradient CH$_2$Cl$_2$/MeOH/NH$_4$OH 80/20/1) in order to lead to the expected product (23 mg, 0.044 mmol, 11%) as a mixture of N1/N2 isomers in a ratio of about 1/2.

N2 Isomer:

MS (ES (+)): m/z [M+H]$^+$=447

$^1$H NMR (400 MHz, DMSO-d$_6$): δ (ppm)=1.41 (s, 9H, C(CH$_3$)$_3$), 3.24-3.32 (m, 4H, N—CH$_2$—CH—N, N—CH—CH$_2$—NHBoc), 4.36 (m, 1H, N—CH—CH$_2$—NHBoc), 4.67 (m, 1H, N—CH$_2$—CH—N), 4.69 (s, 2H, CH$_2$CONH$_2$), 7.02 (m, 1H, NHBOC), 7.40 (s, 2H, NH$_2$), 7.65 (s, 1H, pyrazole).

Ion exchange is achieved on a DOWEX 50WX8 resin (4 g) as indicated in stage B of Example 7 in order to afford after freeze-drying the expected sodium salt (17 mg, 0.126 mmol, 35%) as a beige powder.

MS (ES (−)): m/z [M−H]$^-$=445

Stage C

Sodium trifluoroacetate salt of trans-8-(aminomethyl)-5,6-dihydro-6-oxo-5-(sulfooxy)-4H-4,7-methano-pyrazolo[3,4-e][1,3]diazepine-2(8H)acetamide The compound obtained in stage B (17 mg, 0.036 mmol) is suspended in anhydrous dichloromethane (0.07 mL), under nitrogen. Trifluoroacetic acid (0.027 mL) is then added dropwise and the reaction is then continued at room temperature for 3 hrs. After dry evaporation, the product is then taken up in water, frozen and freeze-dried in order to lead to the expected product (17 mg, 0.035 mmol, 98%) as a beige solid, as a mixture of N1/N2 isomers in a ratio of about 1/2.

N2 Isomer

MS (ES (−)): m/z [M−H]$^-$=345

$^1$H NMR (400 MHz, MeOD-d$_4$): δ(ppm)=3.31-3.36 (m, 4H, N—CH$_2$—CH—N, N—CH—CH$_2$—NH$_3^+$), 4.60 (m, 1H, N—CH—CH$_2$—NH$_3^+$), 4.71 (m, 1H, N—CH$_2$—CH—N), 4.74 (s, 2H, CH$_2$CONH$_2$), 7.25 (broad s, 1H, NH), 7.45 (broad s, 1H, NH), 7.73 (s, 1H, pyrazole), 8.04 (sl, 1H, NH$_3^+$).

Pharmaceutical Composition

A composition was prepared for injection containing:
Compound of Example 1: 500 mg
Sterile aqueous excipient: q.s.p. 5 cm$^3$ Pharmacological Study of the Compounds of the Invention Activity in vitro, method of dilutions in a liquid medium: A series of tubes is prepared in which the same amount of sterile nutritive medium is distributed, increasing amounts of the product to be studied are distributed in each tube, and each tube is then sown with a bacterial strain. After incubation for 24 hrs in the oven at 37° C., inhibition of growth is appreciated by trans-illumination, which allows determination of the minimum inhibitory concentrations (MICs) expressed in μg/ml.

Thus tests are carried out with the products of Examples 1 to 8 in comparison with products of Examples 7, 9, 11 and 45 of application WO 04/052891. The products of the present application prove to be very active on *Pseudomonas aeruginosa*, which is absolutely not the case of the comparison products. The activity difference on *Pseudomonas aeruginosa* between the products of the invention and the closest products from the prior art is located according to the products in a range from 16 to more than 500.

Activity on *Pseudomonas aeruginosa* (1771 Strain of the wild type)

| Molecule | MIC (μg/mL) 24 h (*P. aerug*, 1771) |
| --- | --- |
| Ex 1 | 0.25 |
| Ex 2 | 2 |
| Ex 3 | 2 |
| Ex 4 | 0.25 |
| Ex 5 | 0.25 |
| Ex 6 | 8 |
| Ex 7 | 4 |
| Ex 8 | 0.5 |
| Ex 7 Patent application WO 04/052891 | >128 |
| Ex 9 Patent application WO 04/052891 | >128 |
| Ex 11 Patent application WO 04/052891 | >128 |
| Ex 45 Patent application WO 04/052891 | >128 |
| IMP | 1 |
| CAZ | 1 |

IMP = Imipenem and CAZ = Ceftazidime. (Results given as indications).

What is claimed is:

1. A compound of formula (I), isomers, diastereoisomers, or combinations thereof, the compound comprising:

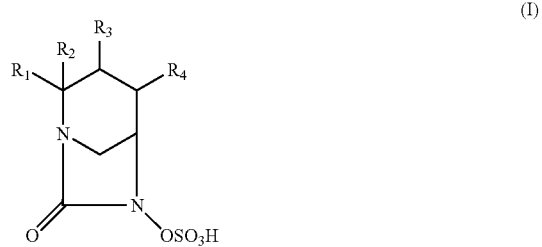

(I)

wherein:

R$_1$ represents a (CH$_2$)$_n$—NH$_2$ radical, n being equal to 1 or 2;

R$_2$ represents a hydrogen atom;

$R_3$ and $R_4$ form together a nitrogen-containing heterocycle with aromaticity with 5 apices containing 1, 2 or 3 nitrogen atoms, substituted on this nitrogen atom or on one of these nitrogen atoms with a $(CH_2)_m$—$(C(O))_p$—$R_5$ group, m being equal to 0, 1, 2 or 3, p being equal to 0 or 1 and R5 representing a hydroxy group, in which case p is equal to 1, or an amino, $(C_1$-$C_6)$alkyl of di-$(C_1$-$C_6)$ alkyl amino group, or a nitrogen-containing heterocycle with aromaticity with 5 or 6 apices containing 1 or 2 nitrogen atoms and, if necessary, an oxygen or sulfur atom;

wherein when the sub-group $(C(O))_p$—R5 forms a carboxy, amino, (C1-C6)alkyl or di(C1-C6)alkyl amino group, m is different from 0 or 1;

wherein the compound is in a free form and/or as zwitterions and salts with pharmaceutically acceptable mineral or organic bases and acids.

2. The compound of general formula (I) according to claim 1, wherein $R_3$ and $R_4$ form together a substituted pyrazolyl radical.

3. The compound of general formula (I) according to claim 1, wherein $R_1$ is a $(CH_2)_n$—$NH_2$ group, n being equal to 1, and the heterocycle formed by $R_3$ and $R_4$ is substituted with a $(CH_2)_m$—$(C(O))_p$—$R_5$ group as defined in claim 1.

4. The compound of general formula (I) according to claim 1, wherein $R_5$ represents an amino, $(C_1$-$C_6)$alkyl or di-$(C_1$-$C_6)$alkyl amino group.

5. The compounds of general formula (I) according to claim 1 selected from the group consisting of:
   trans 8-(aminomethyl)-2-carbamoyle-4,8-dihydro-5-(sulfo-oxy)-4,7-methano-7H-pyrazolo[3,4-e][1,3]diazepin-6(5H)-one,
   trans 8-(aminomethyl)-2-dimethylcarbamoyle-4,8-dihydro-5-(sulfooxy)-4,7-methano-7H-pyrazolo[3,4-e][1,3]diazepin-6(5H)-one,
   trans 8-(aminomethyl)-2-methylcarbamoyle-4,8-dihydro-5-(sulfooxy)-4,7-methano-7H-pyrazolo[3,4-e][1,3]diazepin-6(5H)-one,
   trans 8-(aminomethyl)-1-(2-aminoethyl)-4,8-dihydro-5-(sulfooxy)-4,7-methano-7H-pyrazolo[3,4-e][1,3]diazepin-6(5H)-one,
   trans 8-(aminomethyl)-2-(2-aminoethyl)-4,8-dihydro-5-(sulfooxy)-4,7-methano-7H-pyrazolo[3,4-e][1,3]diazepin-6(5H)-one,
   trans 8-(aminomethyl)-2-(2-pyridinyl)-4,8-dihydro-5-(sulfo-oxy)-4,7-methano-7H-pyrazolo[3,4-e][1,3]diazepin-6(5H)-one,
   trans 8-(aminomethyl)-5,6-dihydro-6-oxo-5-(sulfooxy)-4H-4,7-methanopyrazolo[3,4-e][1,3]diazepin-2(8H)-acetic acid,
   trans 8-(aminomethyl)-5,6-dihydro-6-oxo-5-(sulfooxy)-4H-4,7-methanopyrazolo[3,4-e][1,3]diazepin-2(8H)-acetamide, and combinations thereof;
   in free form and/or as zwitterions and/or salts with pharmaceutically acceptable mineral or organic bases and acids, isomers, diasteroisomers, and combinations thereof.

6. A medicament composition comprising a compound according to claim 1.

7. A pharmaceutical composition comprising an active ingredient comprising a compound according to claim 1.

8. A method for preparing a compound of formula (I), isomers, diasteroisomers, or combinations thereof, represented by:

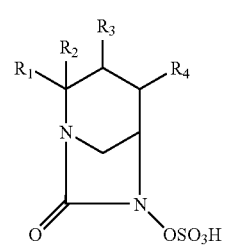

wherein:

$R_1$ represents a $(CH_2)_n$—$NH_2$ radical, n being equal to 1 or 2;

$R_2$ represents a hydrogen atom;

$R_3$ and $R_4$ form together a nitrogen-containing heterocycle with aromaticity with 5 apices containing 1, 2 or 3 nitrogen atoms, substituted on this nitrogen atom or on one of these nitrogen atoms with a $(CH_2)_m$—$(C(O))_p$—$R_5$ group, m being equal to 0, 1, 2 or 3, p being equal to 0 or 1 and $R_5$ representing a hydroxy group, in which case p is equal to 1, or an amino, $(C_1$-$C_6)$alkyl of di-$(C_1$-$C_6)$ alkyl amino group, or a nitrogen-containing heterocycle with aromaticity with 5 or 6 apices containing 1 or 2 nitrogen atoms and, if necessary, an oxygen or sulfur atom;

wherein when the sub-group $(C(O))_p$—R5 forms a carboxy, amino, (C1-C6)alkyl or di(C1-C6)alkyl amino group, m is different from 0 or 1; wherein the compound is in a free form or as zwitterions and salts with pharmaceutically acceptable mineral or organic bases and acids;

the method comprising treating a compound of formula (II) represented by:

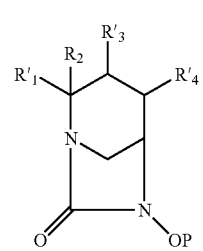

wherein $R'_1$ represents a $(CH_2)_n$—$NH_2$ radical, n being equal to 1 or 2, wherein the nitrogen atom is protected, $R_2$ represents a hydrogen atom, $R'_3$ and $R'_4$ form together a nitrogen-containing heterocycle with aromaticity with 5 apices containing 1, 2 or 3 nitrogen atoms and P represents a group protecting the hydroxy radical, in the presence of a base, with a compound of formula (III):

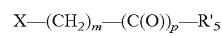

wherein X represents a halogen atom or a OH group which may be activated, m is equal to 0, 1, 2 or 3, and p is equal to 0 or 1, and $R'_5$ represents a radical $R_5$ wherein the reactive amino or carboxy group is if necessary protected, in order to obtain a compound of formula (IV):

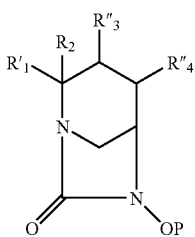

(IV)

wherein R'$_1$, R$_2$ and P are as defined above and R"$_3$ and R"$_4$ form together a nitrogen-containing heterocycle with aromaticity with 5 apices as defined above for R$_3$ and R$_4$, substituted with a (CH$_2$)$_n$—(C(O))$_p$—R'$_5$ group, m, p and R'$_5$ being as defined above, deprotecting the hydroxyl radical, wherein the obtained compound is submitted to sulfatation reaction by action of complexed SO$_3$, wherein the process optionally further comprises subjecting the compound obtained to one or more of the following reactions, in a suitable order:
deprotection of the aminated function(s) and if necessary of the carboxy functions present,
salification,
ion exchange,
resolution or separation of diastereoisomers.

9. A method for preparing a compound of formula (I), isomers, diastereoisomers, or combinations thereof, represented by:

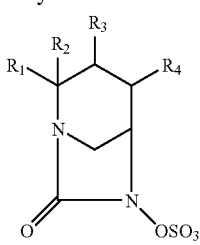

(I)

wherein:
R$_1$ represents a (CH$_2$)$_n$—NH$_2$ radical, n being equal to 1 or 2;
R$_2$ represents a hydrogen atom;
R$_3$ and R$_4$ form together a nitrogen-containing heterocycle with aromaticity with 5 apices containing 1, 2 or 3 nitrogen atoms, substituted on this nitrogen atom or on one of these nitrogen atoms with a (CH$_2$)$_m$—(C(O))$_p$—R$_5$ group, m is equal to 0, p is equal to 1 and R$_5$ represents an amino, (C$_1$-C$_6$)alkyl or di-(C$_1$-C$_6$)alkyl amino group;
wherein the compound is in a free form or as zwitterions and salts with pharmaceutically acceptable mineral or organic bases and acids;
the method comprising treating a compound of formula (II) represented by:

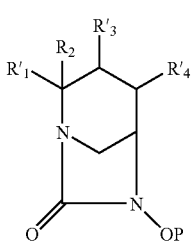

(II)

wherein R'$_1$ represents a (CH$_2$)$_n$—NH$_2$ radical, n being equal to 1 or 2, wherein the nitrogen atom is protected, R$_2$ represents a hydrogen atom, R'$_3$ and R'$_4$ form together a nitrogen-containing heterocycle with aromaticity with 5 apices containing 1, 2 or 3 nitrogen atoms and P represents a group protecting the hydroxy radical; in the presence of a base, with diphosgene, and then with an amine of formula

H—R"$_5$ wherein R"$_5$ represents an amino, (C$_1$-C$_6$) alkyl or di(C$_1$-C$_6$) alkyl amino, in order to obtain a compound of formula (IV'):

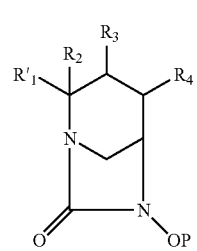

(IV')

wherein R$_3$ and R$_4$ form together a nitrogen-containing heterocycle with aromaticity with 5 apices, substituted with a —C(O)—R"$_5$ group;
deprotecting the hydroxyl radical, wherein the obtained compound is submitted to a sulfatation reaction by action of complexed SO$_3$;
wherein the process optionally further comprises subjecting the compound obtained to one or more of the following reactions, in a suitable order:
deprotection of the aminated function(s) and if necessary of the carboxy functions present,
salification,
ion exchange, or
resolution or separation of diastereoisomers.

10. A compound of formula (I), isomers, diastereoisomers, or combinations thereof, the compound comprising:

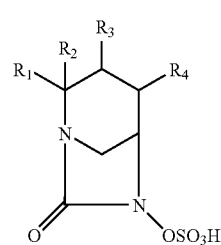

(I)

wherein:
R$_1$ represents a (CH$_2$)$_n$—NH$_2$ radical, n being equal to 1;
R$_2$ represents a hydrogen atom;
R$_3$ and R$_4$ form together a nitrogen-containing heterocycle with aromaticity with 5 apices containing 1, 2 or 3 nitrogen atoms, substituted on this nitrogen atom or on one of these nitrogen atoms with a (CH$_2$)$_m$—(C(O))$_p$—R$_5$ group, m being equal to 0, 1, 2 or 3, p being equal to 0 or 1 and R$_5$ representing a hydroxy group, in which case p is equal to 1, or an amino, (C$_1$-C$_6$)alkyl of di-(C$_1$-C$_6$) alkyl amino group, or a nitrogen-containing heterocycle with aromaticity with 5 or 6 apices containing 1 or 2 nitrogen atoms and, if necessary, an oxygen or sulfur atom;
wherein when the sub-group (C(O))$_p$—R5 forms a carboxy, amino, (C1-C6)alkyl or di(C1-C6)alkyl amino group, m is different from 0 or 1;

wherein the compound is in a free form and/or as zwitterions and salts with pharmaceutically acceptable mineral or organic bases and acids.

11. A compound of formula (I), isomers, diasteroisomers, or combinations thereof, the compound comprising:

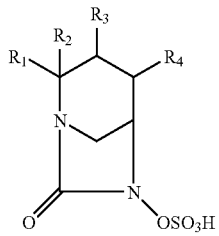

(I)

wherein:

$R_1$ represents a $(CH_2)_n$—$NH_2$ radical, n being equal to 1;

$R_2$ represents a hydrogen atom;

$R_3$ and $R_4$ form together a nitrogen-containing heterocycle with aromaticity with 5 apices containing 1, 2 or 3 nitrogen atoms, substituted on this nitrogen atom or on one of these nitrogen atoms with a $(CH_2)_m$—$(C(O))_p$—$R_5$ group, m being equal to 0, 1, 2 or 3, p being equal to 0 or 1, wherein $R_5$ represents an amino, $(C_1\text{-}C_6)$alkyl or di-$(C_1\text{-}C_6)$alkyl amino group and the sub-group $(C(O))_p$—$R_5$ forms an amino, (C1-C6)alkyl or di(C1-C6)alkyl amino group, m is different from 0 or 1;

wherein the compound is in a free form or as zwitterions and salts with pharmaceutically acceptable mineral or organic bases and acids.

\* \* \* \* \*